(12) United States Patent
Gañán-Calvo

(10) Patent No.: US 6,187,214 B1
(45) Date of Patent: Feb. 13, 2001

(54) METHOD AND DEVICE FOR PRODUCTION OF COMPONENTS FOR MICROFABRICATION

(75) Inventor: Alfonso Gañán-Calvo, Seville (ES)

(73) Assignee: Universidad de Seville, Seville (ES)

( * ) Notice: Under 35 U.S.C. 154(b), the term of this patent shall be extended for 0 days.

(21) Appl. No.: 09/191,784

(22) Filed: Nov. 13, 1998

Related U.S. Application Data

(63) Continuation-in-part of application No. 06/162,061, filed on Oct. 20, 1998, now Pat. No. 6,116,516, which is a continuation-in-part of application No. 09/192,091, filed on Nov. 13, 1998, now Pat. No. 6,116,516.

(30) Foreign Application Priority Data

| May 13, 1996 | (ES) | .................................................. 9601101 |
| Feb. 18, 1997 | (ES) | .......................................... ES/97/00034 |
| Dec. 17, 1997 | (ES) | .................................................. 9702654 |

(51) Int. Cl.$^7$ .............................. C03C 25/68; C23F 1/02; A62C 5/02; A62C 31/02
(52) U.S. Cl. ................................... 216/92; 239/8; 239/10
(58) Field of Search ................................ 216/41, 87–92; 123/445, 467, 470; 239/452, 533.1–533.12; 156/345; 239/8–11

(56) References Cited

U.S. PATENT DOCUMENTS

| 3,700,170 | 10/1972 | Blanka et al. ..................... 239/120.1 |
| 3,804,255 | 4/1974 | Speece .................................. 210/194 |
| 4,141,055 | 2/1979 | Berry et al. .......................... 361/778 |
| 4,162,282 | 7/1979 | Fulwyler et al. ......................... 264/9 |
| 4,347,935 | 9/1982 | Merrill .................................. 209/3.2 |
| 4,352,789 | 10/1982 | Thiel ....................................... 424/46 |
| 4,363,446 | 12/1982 | Jaeggle et al. ........................ 239/453 |
| 4,444,961 | 4/1984 | Timm ..................................... 526/88 |

(List continued on next page.)

FOREIGN PATENT DOCUMENTS

| 563807 | 7/1975 | (CH) . |
| 4031262A1 | 4/1992 | (DE) . |
| 0 249 186 A1 | 12/1987 | (EP) . |
| 0 250 164 A2 | 12/1987 | (EP) . |
| 2255291A | 11/1992 | (GB) . |
| 2099078A | 12/1992 | (GB) . |
| 59-174561A | 10/1984 | (JP) . |
| 03169331 | 7/1991 | (JP) . |
| WO 90/05583 | 5/1990 | (WO) . |
| WO 91/18682 | 12/1991 | (WO) . |
| WO 94/11116 | 5/1994 | (WO) . |
| WO 94/23129 | 10/1994 | (WO) . |
| WO 95/23030 | 8/1995 | (WO) . |
| WO 96/16326 | 5/1996 | (WO) . |
| WO 97/43048 | 11/1997 | (WO) . |
| WO 97/44080 | 11/1997 | (WO) . |

OTHER PUBLICATIONS

Bowden et al., Science 276:233–5 (1997).
Brenn et al., *Chemical Engineering Science*, 52(2):237–244 (Jan. 1997) (Abstract).

(List continued on next page.)

*Primary Examiner*—Jeffrie R Lund
*Assistant Examiner*—Alva C Powell
(74) *Attorney, Agent, or Firm*—Karl Bozicevic; Bozicevic, Field & Francis LLP

(57) ABSTRACT

Atomized particles within a desired size range (e.g., 1 micron to about 5 microns) are produced from two immiscible fluids, a first fluid source containing the formulation to be atomized, and a second fluid source which is contained in a pressure chamber surrounding at least the area where the first liquid is to be provided. The invention provides methods for: the production of templates for microfabrication, such as particles that serve as templates for self-assembly of monolayers; the creation of small particles to serve as building blocks for the microassembly of objects; and the use of an atomizate to etch configurations and/or patterns onto the surface of an object by removing a selected portion of the surface.

13 Claims, 5 Drawing Sheets

U.S. PATENT DOCUMENTS

| | | | |
|---|---|---|---|
| 4,603,671 | 8/1986 | Yoshinaga et al. | 123/467 |
| 4,617,898 | 10/1986 | Gayler | 123/460 |
| 4,628,040 | 12/1986 | Green et al. | 502/9 |
| 4,662,338 | 5/1987 | Itoh et al. | 123/467 |
| 4,717,049 * | 1/1988 | Green et al. | 222/420 |
| 4,781,968 | 11/1988 | Kellerman | 428/209 |
| 4,917,857 | 4/1990 | Jaeckel | 419/9 |
| 5,020,498 | 6/1991 | Linder et al. | 123/450 |
| 5,077,176 | 12/1991 | Baggio et al. | 430/313 |
| 5,087,292 | 2/1992 | Garrido | 75/681 |
| 5,174,247 | 12/1992 | Tosa et al. | 123/25 C |
| 5,180,465 | 1/1993 | Seki et al. | 216/13 |
| 5,194,915 | 3/1993 | Gilby | 356/318 |
| 5,230,850 | 7/1993 | Lewis | 264/112 |
| 5,364,632 | 11/1994 | Benita et al. | 424/450 |
| 5,364,838 | 11/1994 | Rubsamen | 514/3 |
| 5,372,867 | 12/1994 | Hasegawa et al. | 428/141 |
| 5,397,001 | 3/1995 | Yoon et al. | 207/170 |
| 5,404,871 | 4/1995 | Goodman et al. | 128/200.14 |
| 5,458,292 | 10/1995 | Hapeman | 239/533.4 |
| 5,522,385 | 6/1996 | Lloyd et al. | 128/203.26 |
| 5,554,646 | 9/1996 | Cook et al. | 514/560 |
| 5,597,491 | 1/1997 | Winkler | 210/754 |
| 5,697,341 | 12/1997 | Ausman et al. | 123/446 |
| 5,740,794 | 4/1998 | Smith et al. | 128/203.15 |
| 5,770,095 * | 6/1998 | Sasaki et al. | 216/38 |
| 5,775,320 | 7/1998 | Patton et al. | 128/200.14 |
| 5,958,111 * | 9/1999 | Willeke et al. | 95/268 |

OTHER PUBLICATIONS

Borchardt et al., *Chemistry & Biology*, 4(12):961–968 (1997).

Chin et al., *Trans. ASME J. Eng. Gas Turbines Power*, 106:639–644 (1983).

Cloupeau et al. (1989), *J. Electrostat* 22:135–159.

Fernández de la Mora et al. (1994), *J. Fluid Mech.* 260:155–184.

Forbes et al., *J. Austral. Math. Soc. Ber. B.*, 32:231–249 (1990).

Gañán–Calvo et al. (1997), *J. Aerosol Sci.* 28:249–275.

Gauthier, *Optics & Laser Technology*, 29(7): 389–399 (Oct. 1997).

Hartman et al. (1997), "Electrohydrodynamic Atomization in the Cone–Jet Mode," Paper presented at the ESF Workshop on Electrospray, Sevilla, Feb. 28–Mar. 1, 1997 [see also the papers contained in the Special Issue for Electrosprays (1994)].

Huck et al., *Journal of American Chemical Society* pp. 8267–8268 (1998).

Jasuja, *ASME Paper* 82–GT–32 (1982).

Liu et al. (1974), *J. Coloid Interface Sci.* 47:155–171.

Lorenzetto et al., *AIAA J.*, 15:1006–1010 (1977).

Nukiyama et al., *Trans. Soc. Mech. Eng. Jpn.*, 5:68–75 (1939).

Lord Rayleigh (1879), *Proc. London Math. Soc. 10*:4–13.

Service et al., (1997), *Science*, 277:1199–1200.

Singler et al., *Phys. Fluids A*, 5:1156–1166 (1993).

Tuck et al., *J. Austral. Math. Soc. Ser. B.*, 25:433–450 (1984).

Ünal, *Metall. Trans. B.*, 20B:613–622 (1989).

Whitesides et al., *Sciences* 254:1312–9 (1991).

Wigg, *J. Inst. Fuel*, 27:500–505 (1964).

Winfree et al., *Nature*, 394539–44 (1998).

* cited by examiner

METHOD AND DEVICE FOR PRODUCTION OF COMPONENTS FOR MICROFABRICATION

CROSS-REFERENCES

This application is a continuation-in-part of U.S. application Ser. No. 09/192,091, filed on Nov. 13, 1998 now U.S. Pat. No. 6,116,516, which is a continuation-in-part of U.S. application Ser. No. 09/171,518 filed on Oct. 20, 1998 now, U.S. Pat. No. 6,119,953. Further, this application claims priority to Spanish Application No. P9702654 filed Dec. 17, 1997 under 35 U.S.C. §119.

FIELD OF THE INVENTION

This invention relates generally to the field of fabrication, and particularly to the filed of microfabrication.

BACKGROUND OF THE INVENTION

Products constructed using conventional technology are generally built using a "top-down" approach. Top-down refers to the current way of fabricating most of today's products, using large and expensive machines to manipulate matter in bulk. While miniaturization of devices using top-down technology has increased performance and efficiency, the use of top-down technology to miniaturize devices becomes increasingly difficult and expensive with the decrease in the size of the fabricated object. For instance, conventional techniques for etching circuit patterns, particularly in microcircuits, it is difficult to carry out stable and uniform etching methods when the printed circuits have a width of 0.1 mm or less.

An alternative to top-down technology, a so-called "bottom-up" approach, refers to the fabrication of objects from a set of small, fundamental building blocks, which cannot be reduced further. Complex objects are fabricated by creating and assembling these building blocks using a specified sequence of construction steps. This technique is very similar to creating software, where the building blocks of information (bits) are arranged in useful patterns.

Molecular assembly presents a 'bottom-up' approach to the fabrication of objects specified with incredible precision. Molecular assembly includes construction of objects using tiny assembly components, which can be arranged using techniques such as microscopy, e.g. scanning electron microspray. Microelectrodeposition and microetching can also be used in microfabrication of objects having distinct, patterned surfaces.

Molecular self-assembly is the spontaneous association of molecules under equilibrium conditions into stable, structurally well-defined aggregates joined by noncovalent bonds. Molecular self-assembly is ubiquitous in biological systems and underlies the formation of a wide variety of complex biological structures. Self-assembly is also emerging as a new strategy in chemical synthesis, with the potential of generating nonbiological structures with dimensions as small as 1 to 100 nanometers, and having molecular weights of $10^4$ to $10^{10}$ daltons. Structures even in the upper portion of this range of sizes are presently difficult to attain through chemical synthesis, and the ability to prepare them would open a route to structures comparable in size (and perhaps complementary in function) to those that can be prepared by microlithography and other techniques of microfabrication. G M Whitesides et al., Science 254:1312–9 (1991).

Regular arrays of topologically complex, millimeter-scale objects can also be prepared by self-assembly, with the shapes of the assembling objects and the wettability of their surfaces determining the structure of the arrays. N. Bowden et al., Science 276:233–5 (1997). DNA molecular structures and intermolecular interactions are particularly amenable to the design and synthesis of complex molecular objects, and it has been shown that two-dimensional crystalline forms of DNA can self-assemble from synthetic DNA double-crossover molecules. E Winfree et al., Nature, 394539–44 (1998).

There is a need in the art for a systematic and reproducible method of providing structural components for the fabrication of small objects. There is also a need in the art for a method of modifying very small objects by the directed placement of particles.

SUMMARY OF THE INVENTION

Atomized particles (which may be solid or hollow spheres) within a desired size range (e.g., 0.001 to 100 microns) are produced from a supercritical flow created by two immiscible fluids, a first fluid source containing the formulation to be atomized, and a second fluid source which is contained in a pressure chamber surrounding at least the area where the first liquid is to be provided. Upon presentation of the first fluid source to the second, the second fluid is forced out of an opening positioned in front of the flow path of the formulation. Supercritical flow is obtained when the first and second fluids interact dynamically to form a stable capillary microjet, which in turn results in the formation of a focusing funnel at the opening. Formulation passing through the focusing funnel will atomize upon exiting the opening of the pressurized chamber without physically contacting the perimeter of the opening.

In a first embodiment, the first fluid is forced through a single channel of a feeding needle and expelled out of an exit opening of the needle. The second fluid is forced out of an opening directly in front of the flow path of the formulation being expelled from the feeding needle.

One object of the invention is the production of templates for microfabrication, such as particles that serve as templates for self-assembly of monolayers, the first fluid is preferably a liquid, the second fluid is preferably a liquid immiscible with the first, and the particles are preferably expelled into a liquid that is the same or similar to the second liquid. This creates particles that are suspended in the second fluid, and the liquid interface of the particles provides a surface for the action of microcapillary forces.

Another object of the invention is the creation of small particles to serve as building blocks for the microassembly of objects. One type of particle that may be particularly useful are small, hollow particles composed of a gas nucleus, preferably an air nucleus, and a solid coating.

Another object of the invention is to create an array of small particles using the method of the invention. Particles containing a relatively constant concentration of materials, and conformity of size (e.g. 3 to 30% difference in diameter) from particle to particle, may be dispersed on any appropriate solid support surface.

Another object of the invention is to create particles which each contain a constant amount of a discrete molecule. Such discrete molecules are preferably biological molecules, informatics molecules, and/or energy conversion molecules.

Another object of the invention is liquid is preferably a solution containing a high concentration of solute. Alternatively, the first fluid liquid is a suspension containing a high concentration of suspended matter. In either case, the liquid quickly evaporates upon atomization (due to the small size of the particles formed) to leave very small dry particles.

In a second embodiment of the invention, the first fluid is comprised of a plurality of fluids that are forced through separate channels and expelled out of an exit opening of the needle. The stream of the different fluids contact prior to being expelled to creating a plurality of layers to be atomized. The second fluid is forced out of an opening directly in front of the flow path of the fluids being expelled from the feeding needle.

A feature of the invention is that the method can produce particles each of which are comprised of a plurality of formulations.

An object of the invention is the creation of particles having multiple layers which contain discrete molecules. Such discrete molecules may be present in any of the layers of the formulation, but preferably are within the innermost layer. The discrete molecules may be dissolved or suspended in a liquid, or may be suspended or sublimated in a gas.

In yet a third embodiment of the invention, a planar feeding piece is used to obtain multiple microjets which are expelled through multiple exit ports of a pressure chamber to create multiple atomized streams.

A feature of the invention is that the diameter of the opening from which the fluid is expelled, the diameter of the opening from which gas is expelled, and the distance between these two openings is adjustable to obtain a stable liquid-gas interface which results in a supercritical flow creating a stable capillary jet between the gas and the liquid.

An aspect of the invention is a device and method which produces multiple streams of atomizate thereby quickly atomizing a large amount of formulation.

Another aspect of the invention is the use of an atomizate to etch configurations and/or patterns onto the surface of an object by removing a selected portion of the surface, e.g. to removal of a film coating (i.e. copper) from the surface of a circuit board.

An object of the invention is to provide a method of creating particles of consistent particle size.

Another object of the invention is to provide particles suitable for use in fabrication assembly.

An advantage of the invention is that it consistently produces particles within a desired particle diameter range.

Another advantage of the invention is that the device of the invention is energy efficient in terms of the energy used to create small particles.

Another advantage of the invention is that the method of the invention does not impose size limitations of other methods of creating particles found in the art.

Another advantage of the invention is that it can produce large quantities of particles while expending relatively little energy.

Another advantage of the invention is that the opening from which the fluid is expelled does not accumulate deposits of the formulation.

Another advantage of the invention is that the particles are not prone to agglomeration following dispersion from the opening of the pressure chamber.

Another advantage is that the structure of the device and its use are simple.

These and other aspects, objects, features and advantages will become apparent to those skilled in the art upon reading this disclosure in combination with the figures provided.

BRIEF DESCRIPTION OF THE DRAWINGS

FIG. 3 is a schematic view of yet another embodiment showing a wedge-shaped planar source of formulation.

DETAILED DESCRIPTION OF PREFERRED EMBODIMENTS

Figure 1A:
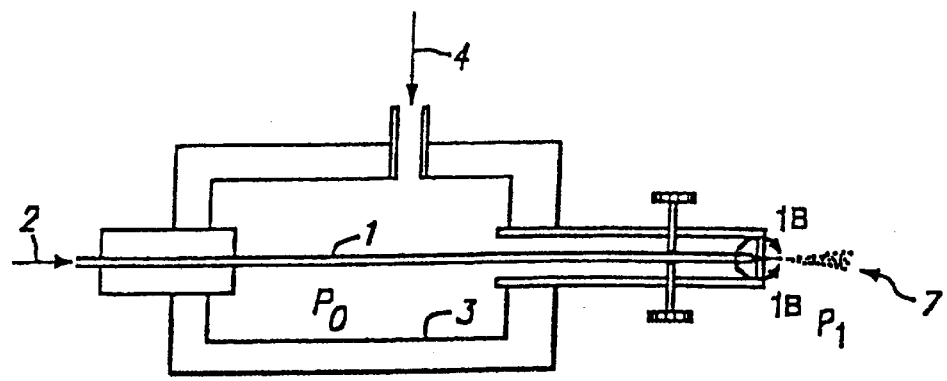
FIG. 1 is a schematic view showing the basic components of one embodiment of the invention with a cylindrical feeding needle as a source of formulation.

Before the present device and method are described, it is to be understood that this invention is not limited to the particular components and steps described, as such may, of course, vary. It is also to be understood that the terminology used herein is for the purpose of describing particular embodiments only, and is not intended to be limiting, since the scope of the present invention will be limited only by the appended claims.

It must be noted that as used herein and in the appended claims, the singular forms "a", "and," and "the" include plural referents unless the context clearly dictates otherwise. Thus, for example, reference to "a particle" includes a plurality of particles and reference to "a discrete component" includes reference to a plurality of discrete components contained within a single particle, and equivalents thereof known to those skilled in the art, and so forth.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and describe the methods and/or materials in connection with which the publications are cited.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Definitions

The terms "particles", "atomized particles" and "atomized particles of formulation" are used interchangeably herein and shall mean particles of formulation that have been atomized using the device and method of the invention. The particles are generally spherical, and may be solid or hollow spheres.

The term "formulation" as used herein refers to any matter which is desired to be atomized. For example, the formulation may be comprised of matter to serve as a template for microfabrication, such as water or perfluorodecalin. In another example, the formulation may contain discrete molecules to be contained within a particle. The formulation is presented in the method of the invention as a component of the first fluid. Formulations are preferably solutions, e.g., aqueous solutions, ethanolic solutions, aqueous/ethanolic solutions, saline solutions, although they may also be colloidal suspensions, microcrystalline suspensions, or emulsions. Formulation may also refer to the matter that will make up a single component of a particle, e.g. either the nucleus or the coating of a multi-layered particle.

The term "smart particle" as used herein refers to particles that have the ability to direct subsequent chemical reactions and/or convert energy from one form to another. Such particles may allow the formation of lines and/or other complex shapes on a surface, interact with other molecules, conduct energy between other molecules. Smart particles can be used for a variety of microfabrication events, for example they may be used as surface growth processes for assembling molecular sensors and for connecting them with nanowires. In another example, smart particles can be used to catalyze biochemical reactions to create molecules and/or components with a desired size, form and function.

The terms "air", "particle free air" and the like, are used interchangeably herein to describe a volume of air which is substantially free of other material and, in particular, free of particles intentionally added such as particles of formulation. The term means that the air does not include particles of formulation which have been intentionally added but is not intended to imply that the normal surrounding air has been filtered or treated to remove all particles although filtering can take place. Air is the preferred gas to use with drug delivery it being noted that other gas, e.g., $CO_2$ can be used.

The term "discrete component" as used herein refers to any small individual component of a formulation that it is desirable to control the number and/or concentration of the individual components within each particle. For example, a "discrete component" may include a biological molecule, e.g. a protein or oligonucleotide, and it may be desirable to have either a selected number of these molecules per particle or a selected concentration of a plurality of these particles in each particle. In another example, a discrete component may be a microdevice, e.g. a sensor chip, and it may be preferable to have a single sensor chip encased in each particle.

The term "assembly component" as used herein refers to any particle produced using the technology of the invention which is structurally designed for use in constructing a larger object. The assembly component may be involved in any aspect of the assembly or construction of an object,, e.g. it may be a structural component of the larger object, it may initiate the reaction resulting in the construction of the larger object, it may functionally control an element used in the production of an element, etc. The assembly component may be multilayered. In addition, an assembly component may comprise a discrete particle or smart particle, preferably in the nucleus of the particle.

The term "etching" as used herein refers to a process whereby a chemical material, preferably a reactive solvent, is used to remove matter from a surface, preferably from a coated surface such as a copper-coated circuit board. Etching can be accomplished by directing solvent particles to a selected portion of the surface area. The solvents should be selected depending on the matter to be removed, e.g. copper may be removed using a solution of ammonia or ammonia salts. The term "microetching" as used herein refers to the process of etching components on a microscale, preferably the etching of materials less than a mm in diameter, more preferably items smaller than 500 microns in diameter.

The term "biological molecule" refers to any biological molecule that occurs in nature, although the biological molecules for use in the present invention need not be derived from its original source and may be produced using other means known in the art such as recombinant technology, biosynthesis, etc. Examples of biological molecules include nucleic acids, both DNA and RNA, oligonucleotides, proteins, peptides, organelles, cellular structures, and whole cells. Biological molecules for use in the invention may be modified for detection, e.g. labeled with radioactivity or fluorescent, and may be stably bound to a surface, i.e. a polymer or bead.

The term biological or "biomimetic molecule" refers to a molecule that is synthetically designed and produced to behave in a manner identical or similar to a biological molecule.

Device in General

The present disclosure focuses on the use of the technology of the present invention in the fabrication of objects, and in particular the use of the technology in the microfabrication of very small objects.

The basic technology of the invention comprises (1) a means for supplying a first fluid; and (2) a pressure chamber supplied with a second fluid. The first fluid may be a liquid, and the second fluid a gas. Alternatively, the first fluid may be a gas and second fluid a liquid or both fluids may be liquid provided the first and second fluid are sufficiently different from each other (immiscible) so as to allow for the formation of a stable microjet of the first fluid moving from the supply means to an exit port of the pressure chamber. Notwithstanding these different combinations of gas-liquid, liquid-gas, and liquid-liquid the invention is generally described with a liquid formulation being expelled from the supply means and forming a stable microjet due to interaction with surrounding air flow focusing the microjet to flow out of an exit of the pressure chamber.

Formation of the microjet and its acceleration and ultimate particle formation are based on the abrupt pressure drop associated with the steep acceleration experienced by the first fluid (e.g., a liquid) on passing through an exit orifice of the pressure chamber which holds the second fluid. On leaving the chamber the flow undergoes a large pressure difference between the first fluid (e.g., a liquid) and the second fluid (e.g., a gas), which in turn produces a highly curved zone on the first fluid (e.g., liquid) surface near the exit port of the pressure chamber and in the formation of a cuspidal point from which a steady microjet flows provided the amount of the first fluid (e.g., the liquid) withdrawn through the exit port of the pressure chamber is replenished. Thus, in the same way that a glass lens or a lens of the eye focuses light to a given point, the flow of the gas surrounds and focuses the liquid into a stable microjet. The focusing effect of the surrounding flow of gas creates a stream of liquid which is substantially smaller in diameter than the diameter of the exit orifice of the pressure chamber. This allows liquid to flow out of the pressure chamber orifice without touching the orifice, providing advantages including (1) clogging of the exit orifice is virtually eliminated, (2) contamination of flow due to contact with substances (e.g. bacteria) on the orifice opening is virtually eliminated, and (3) the diameter of the stream and the resulting particles are smaller than the diameter of the exit orifice of the chamber. This is particularly desirable because it is difficult to precisely engineer holes which are very small in diameter. Further, in the absence of the focusing effect (and formation a stable microjet) flow of liquid out of an opening will result in particles which have about twice the diameter of the exit opening. An additional advantage is that the particles are not prone to agglomeration following exit from the chamber.

Specific embodiments of aerosol creation devices are now described.

Figure 1B:
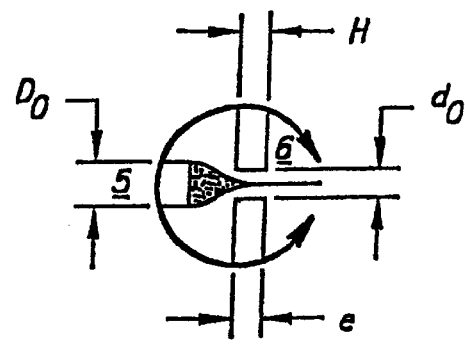

Embodiment of FIG. 1

A first embodiment of the invention where the supply means is a cylindrical feeding needle supplying liquid into a pressurized chamber of gas is described below with reference to FIG. 1.

The components of the embodiment of FIG. 1 are as follows:

1. Feeding needle—also referred to generally as a fluid source and a tube.
2. End of the feeding needle used to insert the liquid to be atomized.
3. Pressure chamber.
4. Orifice used as gas inlet.
5. End of the feeding needle used to evacuate the liquid to be atomized.
6. Orifice through which withdrawal takes place.
7. Atomizate (spray)—also referred to as aerosol.

$D_0$=diameter of the feeding needle; $d_0$=diameter of the orifice through which the microjet is passed; e=axial length of the orifice through which withdrawal takes place; H=distance from the feeding needle to the microjet outlet; $P_0$=pressure inside the chamber; $P_a$=atmospheric pressure.

A device for the production of particles using the technology of the invention will be comprised of at least one source of formulation (e.g., a feeding needle with an opening 2) into which a liquid flowable formulation can be fed and an exit opening 5 from which the formulation can be expelled. The feeding needle 1, or at least its exit opening 5, is encompassed by a pressure chamber 3. The chamber 3 has inlet opening 4 which is used to feed gas into the chamber 3 and an exit opening 6 through which gas from the pressure chamber and liquid formulation from the feeding needle 3 are expelled creating an aerosol.

In FIG. 1, the feeding needle and pressure chamber are configured to obtain a desired result of producing an aerosol wherein the particles are small and uniform in size. Preferably the particles have a size which is in a range of 0.1 to 10 microns, more preferably 1 to 5 microns. Particles of less than 1 micron in diameter can be readily produced via the present invention. The particles of any given aerosol all have about the same diameter with a relative standard deviation of 10% to 30% or more preferably 3% to 20%. Stating that particles of the aerosol have a particle diameter in a range of 1 to 5 microns does not mean that different particles will have different diameters and that some will have a diameter of 1 micron while others of 5 microns. The particles in a given aerosol will all (preferably about 90% or more) have the same diameter ±3% to ±30%. For example, the particles of a given aerosol will have a diameter of 2 microns ±3% to ±10%.

Such a monodisperse aerosol is created using the components and configuration as described above. However, other components and configurations will occur to those skilled in the art. The object of each design will be to supply formulation so that it creates a stable capillary microjet which is accelerated and stabilized by tangential viscous stress exerted by the gas on the liquid surface. The stable microjet created by the gas leaves the area of the pressurized gas (e.g., leaves the pressure chamber and exits the pressure chamber orifice) and splits into particles which have the desired size and uniformity.

The aerosol created is a monodisperse aerosol meaning that the size of the particles produced are relatively uniform in size. The relative standard deviation in particle size is in the range of from about 10% to about 30%, preferably 3% to 10% and most preferably 3% or less. The size of aerosolized particles useful for inhalation is a diameter in the range of from about 0.1 micron to about 10 microns, more preferably about 1 micron to about 3 microns.

For purposes of simplicity the remainder of the detailed description of the operation of the device of FIG. 1 will refer to the first fluid as liquid and the second fluid as gas. The invention is also described herein, however, with other combinations of fluids, e.g. liquid—liquid and gas-liquid. The parameter window used (i.e. the set of special values for the liquid properties, flow-rate used, feeding needle diameter, orifice diameter, pressure ratio, etc.) should be large enough to be compatible with virtually any liquid (dynamic viscosities in the range from $10^{-4}$ to $1$ kg m$^{-1}$s$^{-1}$); in this way, the capillary microjet that emerges from the end of the feeding needle is absolutely stable and perturbations produced by breakage of the jet cannot travel upstream. Downstream, the microjet splits into evenly shaped drops simply by effect of capillary instability (see, for example, Rayleigh, "On the instability of jets", Proc. London Math. Soc., 4–13, 1878), similar in a manner to a laminar capillary jet falling from a half-open tap.

When the stationary, steady interface is created, the capillary jet that emerges from the end of the drop at the outlet of the feeding point is concentrically withdrawn into the nozzle. After the jet emerges from the drop, the liquid is accelerated by tangential sweeping forces exerted by the gas stream flowing on its surface, which gradually decreases the jet cross-section. Stated differently the gas flow acts as a lens and focuses and stabilizes the microjet as it moves toward and into the exit orifice of the pressure chamber.

The forces exerted by the second fluid (e.g., a gas) flow on the first fluid (e.g., a liquid) surface should be steady enough to prevent irregular surface oscillations. Therefore, any turbulence in the gas motion should be avoided; even if the gas velocity is high, the characteristic size of the orifice should ensure that the gas motion is laminar (similar to the boundary layers formed on the jet and on the inner surface of the nozzle or hole).

Stable Capillary Microjet

Figure 4:
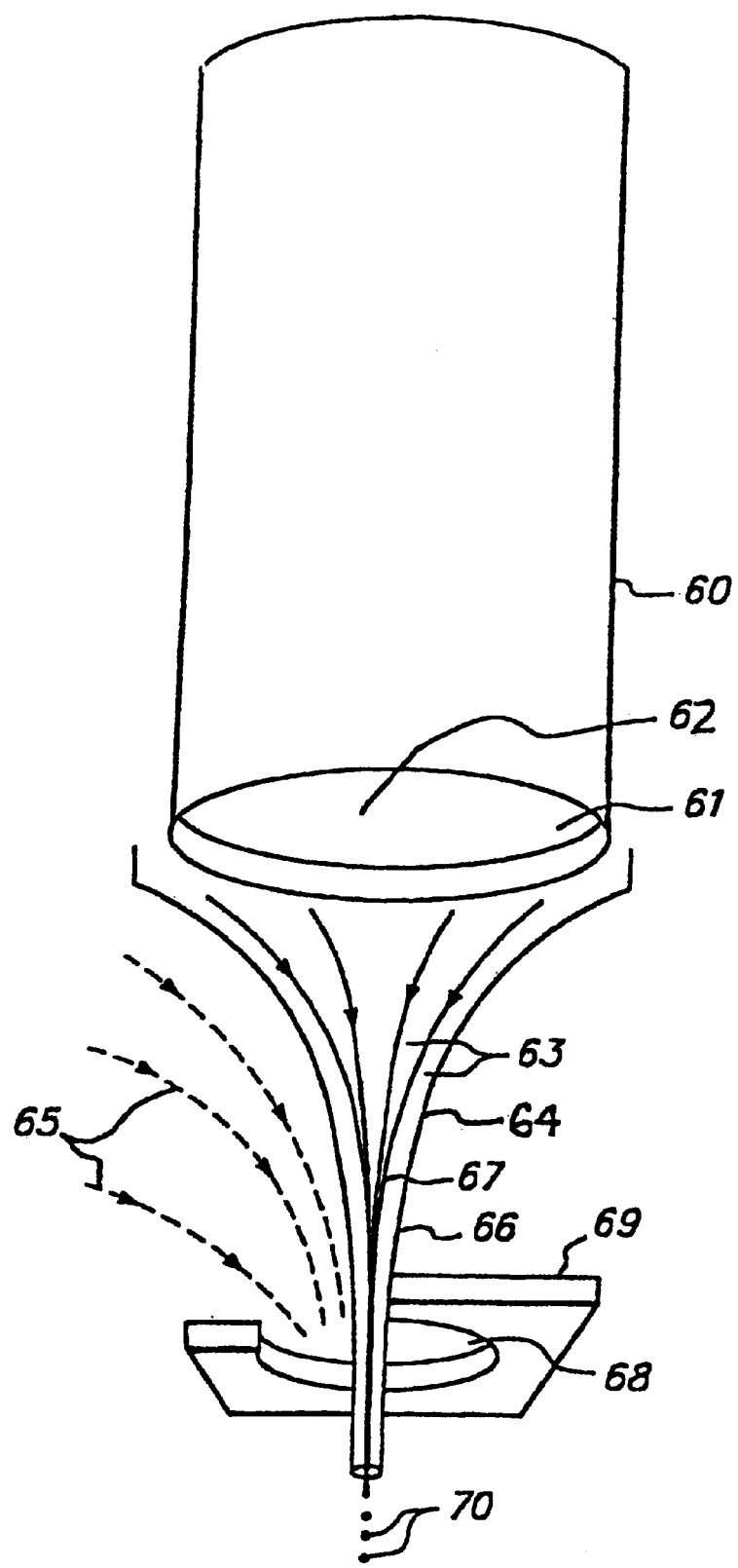
FIG. 4 is a schematic view of a stable capillary microjet being formed and flowing through an exit opening to thereafter form a monodisperse aerosol.
Figure 5:
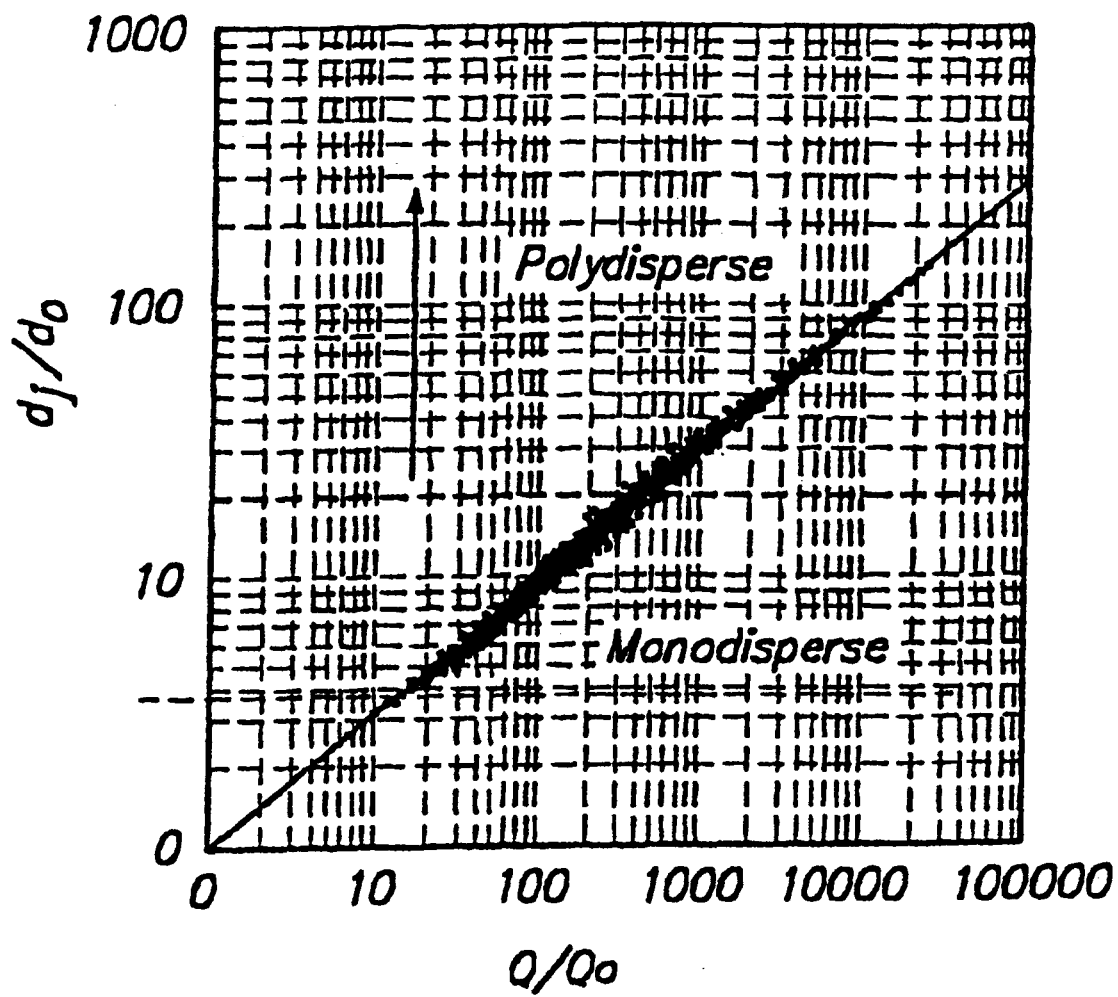
FIG. 5 is a graph of data where 350 measured values of $d_j/d_o$ versus $Q/Q_o$ are plotted.

FIG. 4 illustrates the interaction of a liquid and a gas to form atomizate using the method of the invention. The feeding needle 60 has a circular exit opening 61 with an internal radius $R_0$ which feeds a liquid 62 out of the end, forming a drop with a radius in the range of $R_0$ to $R_0$ plus the thickness of the wall of the needle. The exiting liquid forms an infinite amount of liquid streamlines 63 that interact with the surrounding gas to form a stable cusp at the interface 64 of the two fluids. The surrounding gas also forms an infinite number of gas streamlines 65, which interact with the exiting liquid to create a virtual focusing funnel 66. The exiting liquid is focused by the focusing funnel 66 resulting in a stable capillary microjet 67, which remains stable until it exits the opening 68 of the pressure chamber 69. After exiting the pressure chamber, the microjet begins to break-up, forming monodispersed particles 70.

The gas flow, which affects the liquid withdrawal and its subsequent acceleration after the jet is formed, should be very rapid but also uniform in order to avoid perturbing the fragile capillary interface (the surface of the drop that emerges from the jet).

Liquid flows out of the end of a capillary tube and forms a small liquid drop at the end. The tube has an internal radius $R_o$. The drop has a radius in a range of from $R_o$ to $R_o$ plus the structural thickness of the tube as the drop exits the tube, and thereafter the drop narrows in circumference to a much smaller circumference as is shown in the expanded view of the tube (i.e. feeding needle) 5 as shown in FIGS. 1 and 4.

As illustrated in FIG. 4, the exit opening 61 of the capillary tube 60 is positioned close to an exit opening 68 in a planar surface of a pressure chamber 69. The exit opening 68 has a minimum diameter D and is in a planar member with a thickness L. The diameter D is referred to as a minimum diameter because the opening may have a conical configuration with the narrower end of the cone positioned closer to the source of liquid flow. Thus, the exit opening may be a funnel-shaped nozzle although other opening configurations are also possible, e.g. an hour glass configuration. Gas in the pressure chamber continuously flows out of the exit opening. The flow of the gas causes the liquid drop expelled from the tube to decrease in circumference as the liquid moves away from the end of the tube in a direction toward the exit opening of the pressure chamber.

In actual use, it can be understood that the opening shape which provokes maximum gas acceleration (and consequently the most stable cusp and microjet with a given set of parameters) is a conically shaped opening in the pressure chamber. The conical opening is positioned with its narrower end toward the source of liquid flow.

The distance between the end 61 of the tube 60 and the beginning of the exit opening 68 is H. At this point it is noted that $R_o$, D, H and L are all preferably on the order of hundreds of microns. For example, $R_o$=400 µm, D=150 µm, H=1 mm, L=300 µm. However, each could be 1/100 these sizes.

The end of the liquid stream develops a cusp-like shape at a critical distance from the exit opening 68 in the pressure chamber 69 when the applied pressure drop $\Delta P_g$ across the exit opening 68 overcomes the liquid-gas surface tension stresses $\gamma/R^*$ appearing at the point of maximum curvature—e.g. $1/R^*$ from the exit opening.

A steady state is then established if the liquid flow rate Q ejected from the drop cusp is steadily supplied from the capillary tube. This is the stable capillary cusp which is an essential characteristic of the invention needed to form the stable microjet. More particularly, a steady, thin liquid jet with a typical diameter $d_j$ is smoothly emitted from the stable cusp-like drop shape and this thin liquid jet extends over a distance in the range of microns to millimeters. The length of the stable microjet will vary from very short (e.g. 1 micron) to very long (e.g. 50 mm) with the length depending on the (1) flow-rate of the liquid and (2) the Reynolds number of the gas stream flowing out of the exit opening of the pressure chamber. The liquid jet is the stable capillary microjet obtained when supercritical flow is reached. This jet demonstrates a robust behavior provided that the pressure drop $\Delta P_g$ applied to the gas is sufficiently large compared to the maximum surface tension stress (on the order of $\gamma/d_j$) that act at the liquid-gas interface. The jet has a slightly parabolic axial velocity profile which is, in large part, responsible for the stability of the microjet. The stable microjet is formed without the need for other forces, i.e. without adding force such as electrical forces on a charged fluid. However, for some applications it is preferable to add charge to particles, e.g. to cause the particles to adhere to a given surface. The shaping of liquid exiting the capillary tube by the gas flow forming a focusing funnel creates a cusp-like meniscus resulting in the stable microjet. This is a fundamental characteristic of the invention.

The fluid stream flowing from the tube has substantially more density and develops substantially more inertia as compared to the gas, which has lower viscosity than the liquid. These characteristics contribute to the formation of the stable capillary jet. The stable capillary microjet is maintained stably for a significant distance in the direction of flow away from the exit from the tube. The liquid is, at this point, undergoing "supercritical flow." The microjet eventually destabilizes due to the effect of surface tension forces. Destabilization results from small natural perturbations moving downstream, with the fastest growing perturbations being those which govern the break up of the microjet, eventually creating a uniform sized monodisperse aerosol 70 as shown in FIG. 4.

The microjet, even as it initially destabilizes, passes out of the exit orifice of the pressure chamber without touching the peripheral surface of the exit opening. This provides an important advantage of the invention which is that the exit opening 68 (which could be referred to as a nozzle) will not clog from residue and/or deposits of the liquid. Clogging is a major problem with very small nozzles and is generally dealt with by cleaning or replacing the nozzle. When fluid contacts the surfaces of a nozzle opening some fluid will remain in contact with the nozzle when the flow of fluid is shut off. The liquid remaining on the nozzle surface evaporates leaving a residue. After many uses over time the residue builds up and clogging takes place. The present invention substantially reduces or eliminates this clogging problem.

Mathematics of a Stable Microjet

Cylindrical coordinates (r,z) are chosen for making a mathematical analysis of a stable microjet, i.e. liquid undergoing "supercritical flow." The cusp-like meniscus formed by the liquid coming out of the tube is pulled toward the exit of the pressure chamber by a pressure gradient created by the flow of gas.

The cusp-like meniscus formed at the tube's mouth is pulled towards the hole by the pressure gradient created by the gas stream. From the cusp of this meniscus, a steady liquid thread with the shape of radius r=ξ is withdrawn through the hole by the action of both the suction effect due to $\Delta P_g$, and the tangential viscous stresses $\tau_s$ exerted by the gas on the jet's surface in the axial direction. The averaged momentum equation for this configuration may be written:

$$\frac{d}{d_z}\left[P_l + \frac{\rho_1 Q^2}{2\Pi^2\xi^4}\right] = \frac{2\tau_s}{\xi}, \tag{1}$$

where Q is the liquid flow rate upon exiting the feeding tube, $P_1$ is the liquid pressure, and $\rho_1$ is the liquid density, assuming that the viscous extensional term is negligible compared to the kinetic energy term, as will be subsequently justified. In addition, liquid evaporation effects are neglected. The liquid pressure $P_1$, is given by the capillary equation.

$$P_1 = P_g + \gamma/\xi \quad (2)$$

where $\gamma$ is the liquid-gas surface tension. As shown in the Examples, the pressure drop $\Delta P_g$ is sufficiently large as compared to the surface tension stress $\gamma/\xi$ to justify neglecting the latter in the analysis. This scenario holds for the whole range of flow rates in which the microjet is absolutely stable. In fact, it will be shown that, for a given pressure drop $\Delta P_g$, the minimum liquid flow rate that can be sprayed in steady jet conditions is achieved when the surface tension stress $\gamma/\xi$ is of the order of the kinetic energy of the liquid $\rho_1 Q^2/(2\pi^2\xi^4)$, since the surface tension acts like a "resistance" to the motion (it appears as a negative term in the right-hand side term of Eq. (1)). Thus, $$Q_{min} \sim \left(\frac{\gamma d_j^3}{\rho_1}\right)^{1/2} \quad (3)$$

For sufficiently large flow rates Q compared to $Q_{min}$, the simplified averaged momentum equation in the axial direction can be expressed as $$\frac{d}{d_z}\left(\frac{\rho_1 Q^2}{2\Pi^2\xi^4}\right) = \frac{dP_g}{d_z} + \frac{2\tau_s}{\xi}, \quad (4)$$

where one can identify the two driving forces for the liquid flow on the right-hand side. This equation can be integrated provided the following simplification is made: if one uses a thin plate with thickness L of the order or smaller than the hole's diameter D (which minimizes downstream perturbations in the gas flow), the pressure gradient up to the hole exit is on the average much larger than the viscous shear term $2\tau_s/\xi$ owning to the surface stress. On the other hand, the axial viscous term is of the order $O[\mu^2 Q/D^2 d_j^2]$, since the hole diameter D is actually the characteristic distance associated with the gas flow at the hole's entrance in both the radial and axial directions. This term is very small compared to the pressure gradient in real situations, provided that $\Delta P_g >> \mu^2/D^2 \rho_1$ (which holds, e.g., for liquids with viscosities as large as 100 cpoises, using hole diameters and pressure drops as small as D~10 $\mu$m and $\Delta P_g \geq 100$ mbar). The neglect of all viscous terms in Eq. (4) is then justified. Notice that in this limit on the liquid flow is quasi-isentropic in the average (the liquid almost follows Bernoulli equation) as opposed to most micrometric extensional flows. Thus, integrating (4) from the stagnation regions of both fluids up to the exit, one obtains a simple and universal expression for the jet diameter at the hole exit:

$$d_j \simeq \left(\frac{8\rho_1}{\Pi^2 \Delta P_g}\right)^{1/4} Q^{1/2}, \quad (5)$$

which for a given pressure drop $\Delta P_g$ is independent of geometrical parameters (hole and tube diameters, tube-hole distance, etc.), liquid and gas viscosities, and liquid-gas surface tension. This diameter remains almost constant up to the breakup point since the gas pressure after the exit remains constant.

Monodisperse Particles

Above the stable microjet undergoing "supercritical flow" is described and it can be seen how this aspect of the invention can be made use of in a variety of industrial applications—particularly where the flow of liquid through small holes creates a clogging problem. An equally important aspect of the invention is obtained after the microjet leaves the pressure chamber.

When the microjet exits the pressure chamber the liquid pressure $P_1$ becomes (like the gas pressure $P_g$) almost constant in the axial direction, and the jet diameter remains almost constant up to the point where it breaks up by capillary instability. Defining a Weber number We= $(\rho_g v_g^2 d_j)/\gamma \simeq 2\Delta P_g d_j/\gamma$ (where $v_g$ is the gas velocity measured at the orifice), below a certain experimental value $We_c \sim 40$ the breakup mode is axisymmetric and the resulting droplet stream is characterized by its monodispersity provided that the fluctuations of the gas flow do not contribute to droplet coalescence (these fluctuations occur when the gas stream reaches a fully developed turbulent profile around the liquid jet breakup region). Above this $We_c$ value, sinuous nonaxisymmetric disturbances, coupled to the axisymmetric ones, become apparent. For larger We numbers, the nonlinear growth rate of the sinuous disturbances seems to overcome that of the axisymmetric disturbances. The resulting spray shows significant polydispersity in this case. Thus, it can be seen that by controlling parameters to keep the resulting Weber number to 40 or less, allows the particles formed to be all substantially the same size. The size variation is about ±3% to ±30% and move preferably ±3% to ±10%. These particles can have a desired size e.g. 0.1 microns to 50 microns.

The shed vorticity influences the breakup of the jet and thus the formation of the particles. Upstream from the hole exit, in the accelerating region, the gas stream is laminar. Typical values of the Reynolds number range from 500 to 6000 if a velocity of the order of the speed of sound is taken as characteristic of the velocity of the gas. Downstream from the hole exit, the cylindrical mixing layer between the gas stream and the stagnant gas becomes unstable by the classical Kelvin-Helmholtz instability. The growth rate of the thickness of this layer depends on the Reynolds number of the flow and ring vortices are formed at a frequency of the order of $v_g/D$, where D is the hole diameter. Typical values of $v_g$ and D as those found in our experimental technique lead to frequencies or the order of MHZ which are comparable to the frequency of drop production (of order of $t_b^{-1}$).

Given the liquid flow rate and the hole diameter, a resonance frequency which depends on the gas velocity (or pressure difference driving the gas stream) can be adjusted (tuned) in such a way that vortices act as a forcing system to excite perturbations of a determined wavelength on the jet surface. Experimental results obtained clearly illustrates the different degree of coupling between the two gas-liquid coaxial jets. In one set of experimental results the particle sizes are shown to have a particle size of about 5.7 microns with a standard deviation of 12%. This results when the velocity of the gas has been properly tuned to minimize the dispersion in the size of droplets resulting from the jet breakup. In this case, the flow rate of the liquid jet and its diameter are $0.08\ \mu l\ s^{-1}$ and $3\ \mu m$, respectively. Data have been collected using a MASTERSIZER from MALVERN Instruments. As the degree of coupling decreases, perturbations at the jet surface of different wavelengths become excited and, as it can be observed from the size distributions, dispersion of the spray increases.

It is highly desirable in a number of different industrial applications to have particles which are uniform in size or to create aerosols of liquid particles which are uniform in size. For example, particles for use as an assembly component could have a diameter of 0.1 micron ±3%. In addition, templates for the production of microassemblies may have a diameter of 0.1 micron ±3%. It may is critical that these sizes be uniform, since it is commercially critical that the fabrication of these microassemblies is reproducible.

The gas flow should be laminar in order to avoid a turbulent regime—turbulent fluctuations in the gas flow which have a high frequency and would perturb the liquid-gas interface. The Reynolds numbers reached at the orifice are $$Re = \frac{v_g d_0}{v_g} \sim 4000$$

where $v_g$ is the kinematic viscosity of the gas. Even though this number is quite high, there are large pressure gradients downstream (a highly convergent geometry), so that a turbulent regime is very unlikely to develop.

The essential difference from existing pneumatic atomizers (which possess large Weber numbers) and the present invention is that the aim of the present invention is not to rupture the liquid-gas interface but the opposite, i.e. to increase the stability of the interface until a capillary jet is obtained. The jet, which will be very thin provided the pressure drop resulting from withdrawal is high enough, splits into drops the sizes of which are much more uniform than those resulting from disorderly breakage of the liquid-gas interface in existing pneumatic atomizers.

Both fluids should be fed at a rate ensuring that the system lies within the stable parameter window. Multiplexing is effective when the flow-rates needed exceed those on an individual cell. More specifically, a plurality of feeding sources or feeding needles may be used to increase the rate at which aerosols are created. The flow-rates used should also ensure the mass ratio between the flows is compatible with the specifications of each application.

The gas and liquid can be dispensed by any type of continuous delivery system (e.g. a compressor or a pressurized tank the former and a volumetric pump or a pressurized bottle the latter). If multiplexing is needed, the liquid flow-rate should be as uniform as possible among cells; this may entail propulsion through several capillary needles, porous media or any other medium capable of distributing a uniform flow among different feeding points.

Each individual atomization device should consist of a feeding point (a capillary needle, a point with an open microchannel, a microprotuberance on a continuous edge, etc.) 0.002–2 mm (but, preferentially 0.01–0.4 mm) in diameter, where the drop emerging from the microjet can be anchored, and a small orifice 0.002–2 mm (preferentially 0.01–0.25 mm) in diameter facing the drop and separated 0.01–2 mm (preferentially 0.2–0.5 mm) from the feeding point. The orifice communicates the withdrawal gas around the drop, at an increased pressure, with the zone where the atomizate is produced, at a decreased pressure. The atomizer can be made from a variety of materials (metal, polymers, ceramics, glass).

FIG. 1 depicts a tested prototype where the liquid to be atomized is inserted through one end of the system 2 and the propelling gas in introduced via the special inlet 4 in the pressure chamber 3. The prototype was tested at gas feeding rates from 100 to 2000 mBar above the atmospheric pressure $P_a$ at which the atomized liquid was discharged. The whole enclosure around the feeding needle 1 was at a pressure $P_0>P_a$. The liquid feeding pressure, $P_1$, should always be slightly higher than the gas propelling pressure, $P_o$. Depending on the pressure drop in the needle and the liquid feeding system, the pressure difference ($P_1-P_0>0$) and the flow-rate of the liquid to be atomized, Q, are linearly related provided the flow is laminar—which is indeed the case with this prototype. The critical dimensions are the distance from the needle to the plate (H), the needle diameter ($D_0$), the diameter of the orifice through which the microjet 6 is discharged ($d_0$) and the axial length, e, of the orifice (i.e. the thickness of the plate where the orifice is made). In this prototype, H was varied from 0.3 to 0.7 mm on constancy of the distances ($D_0$=0.45 mm, $d_0$–0.2 mm) and e –0.5 mm. The quality of the resulting spray 7 did not vary appreciably with changes in H provided the operating regime (i e. stationary drop and microjet) was maintained. However, the system stability suffered at the longer H distances (about 0.7 mm). The other atomizer dimensions had no effect on the spray or the prototype functioning provided the zone around the needle (its diameter) was large enough relative to the feeding needle.

Weber Number

Adjusting parameters to obtain a stable capillary microjet and control its breakup into monodisperse particle is governed by the Weber number and the liquid-to-gas velocity ratio or α which equal $V_l/V_g$. The Weber number or "We" is defined by the following equation:

$$We = \frac{\rho_g V_g^2 d}{\gamma}$$

wherein $\rho_g$ is the density of the gas, d is the diameter of the stable microjet, γ is the liquid-gas surface tension, and $V_g^2$ is the velocity of the gas squared.

When carrying out the invention the parameters should be adjusted so that the Weber number is greater than 1 in order to produce a stable capillary microjet. However, to obtain a particle dispersion which is monodisperse (i.e. each particle has the same size ±3 to ±30%) the parameters should be adjusted so that the Weber number is less than 40. The monodisperse aerosol is obtained with a Weber number in a range of about 1 to about 40 when the breaking time is sufficiently small to avoid non-symmetric perturbations. ($1 \leqq We \leqq 40$)

Ohnesorge Number

A measure of the relative importance of viscosity on the jet breakup can be estimated from the Ohnesorge number defined as the ratio between two characteristic times: the viscous time $t_v$ and the breaking time $t_b$. The breaking time $t_b$ is given by [see Rayleigh (1878)]

$$t_b \sim \left(\frac{\rho_l d^2}{\gamma}\right)^{1/2}. \tag{2}$$

Perturbations on the jet surface are propagated inside by viscous diffusion in times $t_v$ of the order of $$t_v \sim \rho_l d^2/\mu_1, \tag{3}$$

where $\mu_1$ is the viscosity of the liquid. Then, the Ohnesorge number, Oh, results $$Oh = \frac{\mu_1}{(\rho_l \gamma d)^{1/2}}. \quad (4)$$

If this ratio is much smaller than unity viscosity plays no essential role in the phenomenon under consideration. Since the maximum value of the Ohnesorge number in actual experiments conducted is as low as $3.7 \times 10^{-2}$, viscosity plays no essential role during the process of jet breakup.

Figure 2:
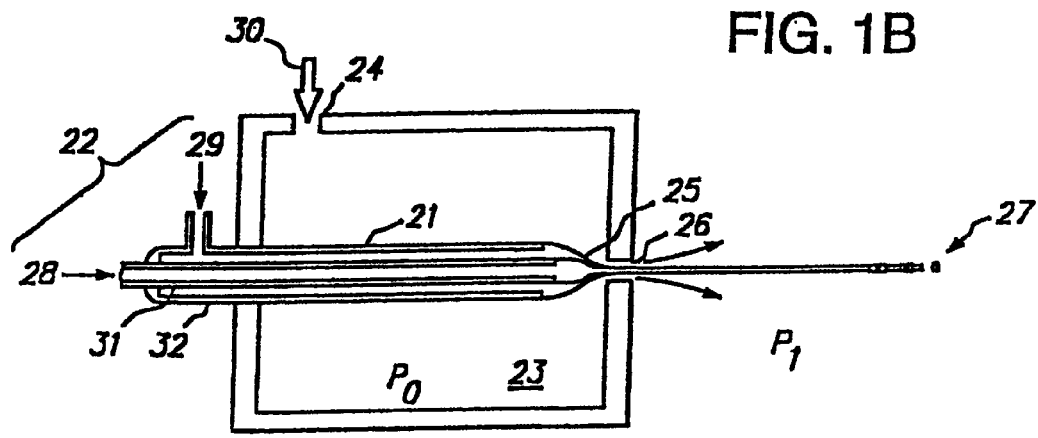
FIG. 2 is a schematic view of another embodiment of the invention with two concentric tubes as a source of formulation.

Embodiment of FIG. 2

A variety of configurations of components and types of fluids will become apparent to those skilled in the art upon reading this disclosure. These configurations and fluids are encompassed by the present invention provided they can produce a stable capillary microjet of a first fluid from a source to an exit port of a pressure chamber containing a second fluid. The stable microjet is formed by the first fluid flowing from the feeding source to the exit port of the pressure chamber being accelerated and stabilized by tangential viscous stress exerted by the second fluid in the pressure chamber on the surface of the first fluid forming the microjet. The second fluid forms a focusing funnel when a variety of parameters are correctly tuned or adjusted. For example, the speed, pressure, viscosity and miscibility of the first and second fluids are chosen to obtain the desired results of a stable microjet of the first fluid focused into the center of a funnel formed with the second fluid. These results are also obtained by adjusting or tuning physical parameters of the device, including the size of the opening from which the first fluid flows, the size of the opening from which both fluids exit, and the distance between these two openings.

The embodiment of FIG. 1 can, itself, be arranged in a variety of configurations. Further, as indicated above, the embodiment may include a plurality of feeding needles. A plurality of feeding needles may be configured concentrically in a single construct, as shown in FIG. 2.

The components of the embodiment of FIG. 2 are as follows:

21. Feeding needle—tube or source of fluid.
22. End of the feeding needle used to insert the liquids to be atomized.
23. Pressure chamber.
24. Orifice used as gas inlet.
25. End of the feeding needle used to evacuate the liquid to be atomized.
26. Orifice through which withdrawal takes place.
27. Atomizate (spray) or aerosol.
28. First liquid to be atomized (inner core of particle).
29. Second liquid to be atomized (outer coating of particle).
30. Gas for creation of microjet.
31. Internal tube of feeding needle.
32. External tube of feeding needle.

D=diameter of the feeding needle; d=diameter of the orifice through which the microjet is passed; e=axial length of the orifice through which withdrawal takes place; H=distance from the feeding needle to the microjet outlet; $\gamma$=surface tension; $P_0$=pressure inside the chamber; $P_a$=atmospheric pressure.

The embodiment of FIG. 2 is preferably used when attempting to form a spherical particle of one substance coated by another substance. The device of FIG. 2 is comprised of the same basic component as per the device of FIG. 1 and further includes a second feeding source 32 which is positioned concentrically around the first cylindrical feeding source 31. The second feeding source may be surrounded by one or more additional feeding sources with each concentrically positioned around the preceding source. The outer coating may be used for a variety of purposes, including: coating particles to prevent small particles from sticking together; to obtain a controlled effect of an internal compound (e.g. an electroconductive molecule) inside; and to protect the stability of another compound (e.g. a biological molecule) contained therein.

The process is based on the microsuction which the liquid-gas or liquid—liquid interphase undergoes (if both are immiscible), when said interphase approaches a point beginning from which one of the fluids is suctioned off while the combined suction of the two fluids is produced. The interaction causes the fluid physically surrounded by the other to form a capillary microjet which finally breaks into spherical drops. If instead of two fluids (gas-liquid), three or more are used that flow in a concentric manner by injection using concentric tubes, a capillary jet composed of two or more layers of different fluids is formed which, when it breaks, gives rise to the formation of spheres composed of several approximately concentric spherical layers of different fluids. The size of the outer sphere (its thickness) and the size of the inner sphere (its volume) can be precisely adjusted. This can allow the manufacture of coated particles for a variety of end uses. For example the thickness of the coating can be varied in different manufacturing events to obtain coated particles which have gradually decreasing thicknesses to obtain a controlled release effect of the contents, e.g. a pharmaceutically active drug. The coating could merely prevent the particles from degrading, reacting, or sticking together.

The method is based on the breaking of a capillary microjet composed of a nucleus of one liquid or gas and surrounded by another or other liquids and gases which are in a concentric manner injected by a special injection head, in such a way that they form a stable capillary microjet and that they do not mix by diffusion during the time between when the microjet is formed and when it is broken. When the capillary microjet is broken into spherical drops under the proper operating conditions, which will be described in detail below, these drops exhibit a spherical nucleus, the size and eccentricity of which can be controlled.

In the case of spheres containing two materials, the injection head 25 consists of two concentric tubes with an external diameter on the order of one millimeter. Through the internal tube 31 is injected the material that will constitute the nucleus of the microsphere, while between the internal tube 31 and the external tube 32 the coating is injected. The fluid of the external tube 32 joins with the fluid of tube 31 as the fluids exit the feeding needle, and the fluids (normally liquids) thus injected are accelerated by a stream of gas that passes through a small orifice 24 facing the end of the injection tubes. When the drop in pressure across the orifice 24 is sufficient, the liquids form a completely stationary capillary microjet, if the quantities of liquids that are injected are stationary. This microjet does not touch the walls of the orifice, but passes through it wrapped in the stream of gas or funnel formed by gas from the tube 32. Because the funnel of gas focuses the liquid, the size of the exit orifice 26 does not dictate the size of the particles formed.

When the parameters are correctly adjusted, the movement of the liquid is uniform at the exit of the orifice 26 and the viscosity forces are sufficiently small so as not to alter either the flow or the properties of the liquids; for example, if there are biochemical molecular specimens having a certain complexity and fragility, the viscous forces that would appear in association with the flow through a micro-orifice might degrade these substances.

FIG. 2 shows a simplified diagram of the feeding needle 21, which is comprised of the concentric tubes 30, 31 through the internal and external flows of the fluids 28, 29 that are going to compose the microspheres comprised of two immiscible fluids. The difference in pressures $P_0-P_a$ ($P_0>P_a$) through the orifice 26 establishes a flow of gas present in the chamber 23 and which is going to surround the microjet at its exit. The same pressure gradient that moves the gas is the one that moves the microjet in an axial direction through the hole 26, provided that the difference in pressures $P_0-P_a$ is sufficiently great in comparison with the forces of surface tension, which create an adverse gradient in the direction of the movement.

There are two limitations for the minimum sizes of the inside and outside jets that are dependent (a) on the surface tensions $\gamma 1$ of the outside liquid 29 with the gas 30 and $\gamma 2$ of the outside liquid 29 with the inside liquid 28, and (b) on the difference in pressures $\Delta P = P_0 - P_a$ through the orifice 26. In the first place, the jump in pressures $\Delta P$ must be sufficiently great so that the adverse effects of the surface tension are minimized. This, however, is attained for very modest pressure increases: for example, for a 10 micron jet of a liquid having a surface tension of 0.05 N/m (tap water), the necessary minimum jump in pressure is in the order of 0.05 (N/m)/0.00001 m=$\Delta P$=50 mBar. But, in addition, the breakage of the microjet must be regular and axilsymmetric, so that the drops will have a uniform size, while the extra pressure $\Delta P$ cannot be greater than a certain value that is dependent on the surface tension of the outside liquid with the gas $\gamma 1$ and on the outside diameter of the microjet. It has been experimentally shown that this difference in pressures cannot be greater than 20 times the surface tension $\gamma 1$ divided by the outside radius of the microjet.

Therefore, given some inside and outside diameters of the microjet, there is a range of operating pressures between a minimum and a maximum; nonetheless, experimentally the best results are obtained for pressures in the order of two to three times the minimum.

The viscosity values of the liquids must be such that the liquid with the greater viscosity $\mu_{max}$ verifies, for a diameter d of the jet predicted for this liquid and a difference through the orifice $\Delta P$, the inequality:

$$\mu_{max} \leq \frac{\Delta P d^2 D}{Q}$$

With this, the pressure gradients can overcome the extensional forces of viscous resistance exerted by the liquid when it is suctioned toward the orifice.

Moreover, the liquids must have very similar densities in order to achieve the concentricity of the nucleus of the microsphere, since the relation of velocities between the liquids moves according to the square root of the densities $v1/v2=(\rho 2/\rho 1)^{1/2}$ and both jets, the inside jet and the outside jet, must assume the most symmetrical configuration possible, which does not occur if the liquids have different velocities (FIG. 2). Nonetheless, it has been experimentally demonstrated that, on account of the surface tension $\gamma 2$ between the two liquids, the nucleus tends to migrate toward the center of the microsphere, within prescribed parameters.

When two liquids and gas are used on the outside, the distance between the planes of the mouths of the concentric tubes can vary, without the characteristics of the jet being substantially altered, provided that the internal tube 31 is not introduced into the external one 32 more than one diameter of the external tube 32 and provided that the internal tube 31 does not project more than two diameters from the external tube 32. The best results are obtained when the internal tube 31 projects from the external one 32 a distance substantially the same as the diameter of the internal tube 31. This same criterion is valid if more than two tubes are used, with the tube that is surrounded (inner tube) projecting beyond the tube that surrounds (outer tube) by a distance substantially the same as the diameter of the first tube.

The distance between the plane of the internal tube 31 (the one that will normally project more) and the plane of the orifice may vary between zero and three outside diameters of the external tube 32, depending on the surface tensions between the liquids and with the gas, and on their viscosity values. Typically, the optimal distance is found experimentally for each particular configuration and each set of liquids used.

Figure 3B:
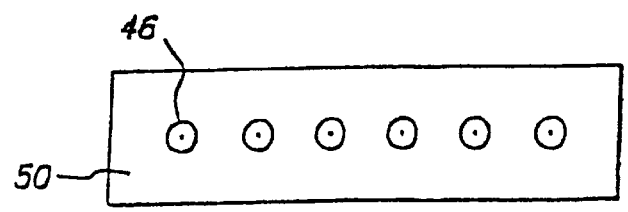
FIG. 3b show a frontal view of the openings in the pressure chamber, with the multiple openings through which the atomizate exits the device.
Figure 3A:
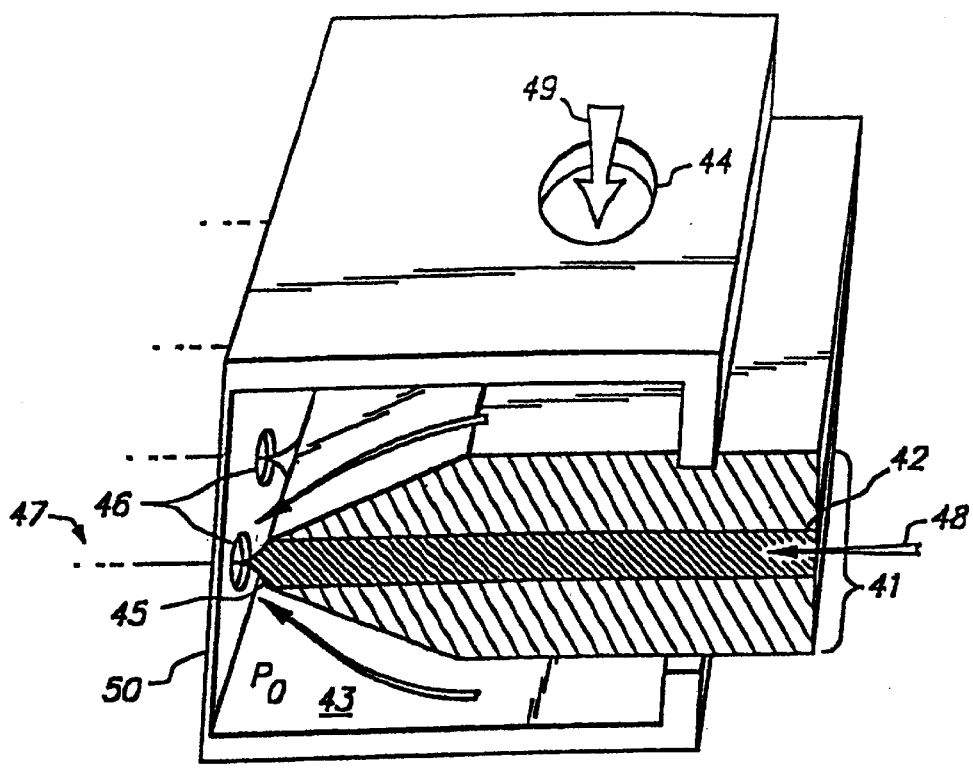
FIG. 3a illustrates a cross-sectional side view of the planar feeding source and the interaction of the fluids.
Figure 3C:
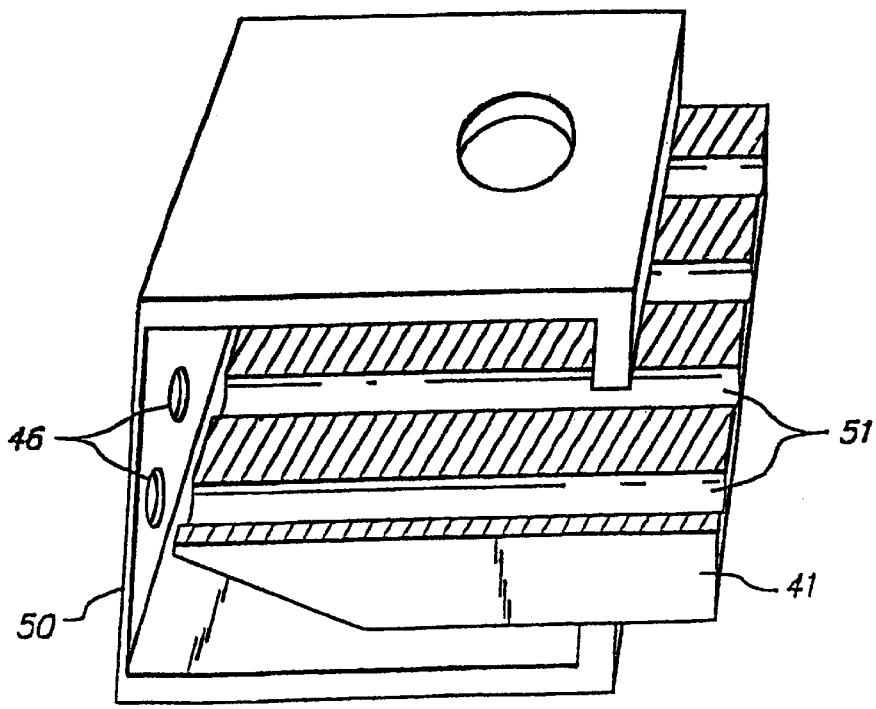
FIG. 3c illustrates the channels that are optionally formed within the planar feeding member. The channels are aligned with the openings in the pressure chamber.

The proposed atomizing system obviously requires fluids that are going to be used in the resulting particle production have certain flow parameters. Accordingly, flows for this use must be:

Flows that are suitable so that the system falls within the parametric window of stability. Multiplexing (i.e. several sets of concentric tubes) may be used, if the flows required are greater than those of an individual cell.

Flows that are suitable so that the mass relation of the fluids falls within the specifications of each application. Of course, a greater flow of gas may be supplied externally by any means in specific applications, since this does not interfere with the functioning of the atomizer.

If the flows are varied, the characteristic time of this variation must be less than the hydrodynamic residence times of liquid and gas in the microjet, and less than the inverse of the first natural oscillation frequency of the drop formed at the end of the injection needle.

Therefore, any means for continuous supply of gas (compressors, pressure deposits, etc.) and of liquid (volumetric pumps, pressure bottles) may be used. If multiplexing is desired, the flow of liquid must be as homogeneous as possible between the various cells, which may require impulse through multiple capillary needles, porous media, or any other medium capable of distributing a homogeneous flow among different feeding points.

Each atomizing device will consist of concentric tubes 31, 32 with a diameter ranging between 0.05 and 2 mm, preferably between 0.1 and 0.4 mm, on which the drop from which the microjet emanates can be anchored, and a small orifice (between 0.001 and 2 mm in diameter, preferably between 0.1 and 0.25 mm), facing the drop and separated from the point of feeding by a distance between 0.001 and 2 mm, preferably between 0.2 and 0.5 mm. The orifice puts the suction gas that surrounds the drop, at higher pressure, in touch with the area in which the atomizing is to be attained, at lower pressure.

Embodiment of FIG. 3

The embodiments of FIGS. 1 and 2 are similar in a number of ways. Both have a feeding piece which is preferably in the form of a feeding needle with a circular exit opening. Further, both have an exit port in the pressure chamber which is positioned directly in front of the flow path of fluid out of the feeding source. Precisely maintaining the alignment of the flow path of the feeding source with the exit port of the pressure chamber can present an engineering challenge particularly when the device includes a number of feeding needles. The embodiment of FIG. 3 is designed to simplify the manner in which components are aligned. The embodiment of FIG. 3 uses a planar feeding piece (which by virtue of the withdrawal effect produced by the pressure difference across a small opening through which fluid is passed) to obtain multiple microjets which are expelled through multiple exit ports of a pressure chamber thereby obtaining multiple aerosol streams. Although a single planar feeding member as shown in FIG. 3 it, of course, is possible to produce a device with a plurality of planar feeding members where each planar feeding member feeds fluid to a linear array of outlet orifices in the surrounding pressure chamber. In addition, the feeding member need not be strictly planar, and may be a curved feeding device comprised of two surfaces that maintain approximately the same spatial distance between the two pieces of the feeding source. Such curved devices may have any level of curvature, e.g. circular, semicircular, elliptical, hemi-elliptical etc.

The components of the embodiment of FIG. 3 are as follows:

41. Feeding piece.
42. End of the feeding piece used to insert the fluid to be atomized.
43. Pressure chamber.
44. Orifice used as gas inlet.
45. End of the feeding needle used to evacuate the liquid to be atomized.
46. Orifices through which withdrawal takes place.
47. Atomizate (spray) or aerosol.
48. first fluid containing material to be atomized.
49. second fluid for creation of microjet.
50. wall of the propulsion chamber facing the edge of the feeding piece.
51. channels for guidance of fluid through feeding piece.

$d_j$=diameter of the microjet formed; $\rho_A$=liquid density of first fluid (48); $\rho_B$=liquid density of second fluid (49); $v_A$=velocity of the first liquid (48); $v_B$=velocity of the second liquid (49); e=axial length of the orifice through which withdrawal takes place; H=distance from the feeding needle to the microjet outlet; $P_0$=pressure inside the chamber;

$\Delta p_g$=change in pressure of the gas; $P_a$=atmospheric pressure; Q=volumetric flow rate.

The proposed dispersing device consists of a feeding piece 41 which creates a planar feeding channel through which a where a first fluid 48 flows. The flow is preferably directed through one or more channels of uniform bores that are constructed on the planar surface of the feeding piece 41. A pressure chamber 43 that holds the propelling flow of a second liquid 49, houses the feeding piece 41 and is under a pressure above maintained outside the chamber wall 50. One or more orifices, openings or slots (outlets) 46 made in the wall 52 of the propulsion chamber face the edge of the feeding piece. Preferably, each bore or channel of the feeding piece 41 has its flow path substantially aligned with an outlet 46.

Formation of the microjet and its acceleration are based on the abrupt pressure drop resulting from the steep acceleration undergone by the second fluid 49 on passing through the orifice 46, similarly to the procedure described above for embodiments of FIGS. 1 and 2 when the second fluid 49 is a gas.

When the second fluid 49 is a gas and the first fluid 48 is a liquid, the microthread formed is quite long and the liquid velocity is much smaller than the gas velocity. In fact, the low viscosity of the gas allows the liquid to flow at a much lower velocity; as a result, the microjet is actually produced and accelerated by stress forces normal to the liquid surface, i.e. pressure forces. Hence, one effective approximation to the phenomenon is to assume that the pressure difference established will result in the same kinetic energy per unit volume for both fluids (liquid and gas), provided gas compressibility effects are neglected. The diameter $d_j$ of the microjet formed from a liquid density $\rho_1$ that passes at a volumetric flow-rate Q through an orifice across which a pressure difference $\Delta P_g$ exists will be given by $$d_j \cong \left(\frac{8\rho_l}{\pi^2 \Delta P_g}\right)^{1/4} Q^{1/2}$$

See Gañán-Calvo, *Physical Review Letters*, 80:285–288 (1998).

The relation between the diameter of the microjet, $d_j$, and that of the resulting drops, $\bar{d}$, depends on the ratio between viscous forces and surface tension forces on the liquid on the one hand, and between dynamic forces and surface tension forces on the gas on the other (i.e. on the Ohnesorge and Weber numbers, respectively) (Hinds (*Aerosol Technology*, John & Sons, 1982), Lefevre (*Atomization and Sprays*, Hemisphere Pub. Corp., 1989) and Bayvel & Orzechowski (*Liquid Atomization*, Taylor & Francis, 1993)). At moderate to low gas velocities and low viscosities the relation is roughly identical with that for capillarity instability developed by Rayleigh:

$$\bar{d} = 1.89 d_j$$

Because the liquid microjet is very long, at high liquid flow-rates the theoretical rupture point lies in the turbulent zone created by the gas jet, so turbulent fluctuations in the gas destabilize or rupture the liquid microjet in a more or less uneven manner. As a result, the benefits of drop size uniformity are lost.

On the other hand, when the second fluid 49 is a liquid and the first fluid 48 is a gas, the facts that the liquid is much more viscous and that the gas is much less dense virtually equalize the fluid and gas velocities. The gas microthread formed is much shorter; however, because its rupture zone is almost invariably located in a laminar flowing stream, dispersion in the size of the microbubbles formed is almost always small. At a volumetric gas flow-rate $Q_g$ and a liquid overpressure $\Delta P_1$, the diameter of the gas microjet is given by $$d_j \cong \left(\frac{8\rho_l}{\pi^2 \Delta P_l}\right)^{1/4} Q_g^{1/2}$$

The low liquid velocity and the absence of relative velocities between the liquid and gas lead to the Rayleigh relation between the diameters of the microthread and those of the bubbles (i.e. $d=1.89 d_j$).

If both fluids 48, 49 are liquid and scarcely viscous, then their relative velocities will be given by $$\frac{v_A}{v_B} = \left(\frac{\rho_B}{\rho_A}\right)^{1/2}$$

The diameter of a microjet of the first liquid at a volumetric flow-rate of A $Q_A$ and an overpressure of B$\Delta P_B$ will be given by $$d_j \cong \left(\frac{8\rho_A}{\pi^2 \Delta P_B}\right)^{1/4} Q_A^{1/2}$$

At viscosities such that the velocities of both fluids 48, 49 will rapidly equilibrate in the microjet, the diameter of the microjet of the first liquid will be given by $$d_j \cong \left(\frac{8\rho_B}{\pi^2 \Delta P_B}\right)^{1/4} Q_A^{1/2}$$

The proposed methods for creating particles requires delivery of the fluids 48, 49 to be used in the dispersion process at appropriate flow-rates. Thus:

(1) Both flow-rates should be adjusted for each separate production method so that they lie within the stable parameter window.
(2) The mass ratio between the flows should be compatible with the specifications of each application. Obviously, fluid flow-rate can be increased by using an external means in special applications.
(3) If the flow-rates are altered, the characteristic time for the variation should be shorter than the hydrodynamic residence times for the liquid and gas in the microjet, and smaller than the reciprocal of the first natural oscillation frequency of the drop formed at the end of the feeding piece.
(4) Therefore, the gas and liquid can be dispensed by any type of continuous delivery system (e.g. a compressor or a pressurized tank the former and a volumetric pump or a pressurized bottle the latter).

Self-Assembled Monolayers

Formulations of different solutions, suspensions and emulsions can be used in the method of the invention to create templates for self-assembled monolayers (SAMs) For example, SAMs formed on the adsorption of long-chain alkanethiols to the surface of gold or alkylsilanes to hydroxylated surfaces are well-ordered organic surfaces that permit control over the properties of the interface at the molecular scale. The ability to present molecules, peptides, and proteins at the interface make SAMs especially useful for fundamental studies of protein adsorption and cell adhesion.

Although photolithography is currently the principal technique used to make microstructures, it has limitations: it cannot easily form non-planar or three dimensional structures; it generates structures that are metastable, and it can only be used for a limited set of materials. Thus, other methods of microproduction are needed to expand the potential uses of microfabrication.

Microcontact printing is a simple technique that can pattern the formation of SAMs in the plane of the monolayer with dimensions on the micron scale. The convenience and broad application offered by SAMs and microcontact printing make this combination of techniques useful for studying a variety of fundamental phenomena in biointerfacial science. M. Mrksich, *Annu Rev Biophys Biomol Struct*, 25:55–78 (1996). Three dimensional (3D) microfabrication microcontact printing (m$\mu$CP) has been used to produce patterned self-assembled monolayers (SAMs) with submicrometer features on curved substrates with radii of curvature as small as 25 micrometers. Wet-chemical etching that uses the patterned SAMs to transfer the patterns formed by m$\mu$CP into gold. R J Jackman et al, *Science*, 269:664 (1995). Such microcontact printing provides an effective and rapid method for routine production of patterned self-assembled monolayers for a variety of uses, including the direction of cell attachment and alteration of cell morphology. P. M. St. John, *J. Neurosci Methods*, 75:171–7 (1997).

Two concepts that direct self assembly, snape recognition and the minimization of liquid-liquid interfacial free energies, can be used to assemble millimeter and micron scale components. The application of self-assembled monolayer molecular films to the surfaces of components can render those components hydrophobic or hydrophilic, depending on the terminal groups of the bound molecules. In an aqueous solution, hydrophobic surfaces bearing a thin film of a hydrophobic, lubricating liquid adhere to similar surfaces with complementary shapes, while being able to adjust their own relative alignment to ensure a proper fit. Components can thus assemble into well-defined aggregates, and can permanently aggregate if the hydrophobic film comprises a curable adhesive. A. Terfort et al., *Nature*, 386:162–164 (1997).

In one example, components can thus be directed in the first fluid of the invention, and the second fluid can be a hydrophobic fluid immiscible with the first fluid. For example, components containing both a hydrophobic and hydrophilic regions, such as a treated polymer, can be dissolved or suspended in an aqueous solution or a gas. A hydrophobic compound, such as an alkane or a photopolymerizable adhesive, and preferably dodecyl methacrylate can be used as the immiscible fluid. Upon particle formation, the hydrophobic solution will coat the component. If the particles are dispersed in water upon dispersion of the particles, a thin layer of the hydrophobic solution will remain surrounding each individual component. The water will displace the hydrophobic liquid from the hydrophilic surfaces of the component, while a thin layer of hydrophobic solution will remain covering the hydrophobic regions. If the particles are then agitated to come into contact with one another, the hydrophobic regions can adhere to one another. The liquid will act as a lubricant, allowing components to adjust their positions relative to one another to minimize the surface area of the hydrophobic liquid-water interface. If the hydrophobic liquid is curable, e.g. a photopolymerizable adhesive, the assembly can be permanently fixed after reaching equilibrium by curing the hydrophobic solution, e.g. applying ultraviolet radiation. Otherwise, a mechanism such as the addition of electromagnetic energy or electrochemical welding may be employed to create a permanent structure from the assembly.

Three-dimensional SAMs can also be created using the methods of the invention by utilizing the surface of a liquid particle as a template for creating microstructures. For example, in the production of a microscale metal structure, the process used for microfabrication of such a structures will depend on: (1) the creation of a particle, preferably a liquid particle, to act as a template for the structure; (2) capillary forces that will allow self-assembly at a liquid-liquid interface on the particle; and (3) microelectrodeposition of a metallic solution on the particle to form and weld together the small, regular metallic structural components.

At present, a preferred method for assembling the microstructures uses capillary forces can be found in the reference Huck et al., *J. Am. Chem. Soc.* 120:8267–8268 (1998), which is incorporated herein by reference. Huck et al. describes the microfabrication of a spherical lattice using as a template either a droplet of water suspended in heptane or a droplet of perfluorodecalin suspended in water. In addition to the creation of spherical structures, such a method may be used to create microelectronic devices, photonic band-gap crystals, biomimetic structures, and the like. Particle production using the method and device of the invention is ideal for the production of micro- and/or nanostructures, since the particle size is extremely reproducible, and the particles are not prone to agglomeration following expulsion from the pressure chamber. Particles to be used as a template can be formed and expelled in to an immiscible liquid.

In another example, an aqueous solution may be used as the first fluid in the invention, and the particles produced may be expelled into an organic liquid. The organic liquid may be any liquid that is immiscible with the aqueous solution, and more preferably is a liquid that can be dissolved in alcohol, ether and/or chloroform. One example of such liquids is a hydrocarbon from petroleum such as heptane, butane, propane, etc. Other compounds that are preferred are organic solvents such as benzene and chlorobenzene. Other immiscible liquids that may be of use in the invention will be known to those skilled in the art. In another example, a hydrophobic liquid may be atomized into an aqueous solution. An organic liquid, and more preferably a biologically inert fluorocarbon such as perfluorodecalin, may be used as the template particle.

In an embodiment of the invention directed to the use of particles as templates for microfabrication, the atomizate is preferably expelled into a same or similar fluid which is used in the production of the stable cusp, i.e. the atomizate made of fluid 1 is expelled into fluid 2 or a fluid similar to fluid 2. Since the particles produced from the method of the invention retain a coating of fluid 2, expulsion into the same liquid will enable the particles to assimilate more readily into the fluid outside the device. Thus, a particle of perfluorodecalin produced using water as the second immiscible fluid of the invention is preferably expelled into water directly following atomization. In another example, an atomizate of water produced in the method of the invention with heptane as the immiscible fluid is preferably expelled from the device in an aqueous solution.

Production of Assembly Components

The method of the invention can also be used to create particles, e.g. hollow spheres, for use as assembly components in microfabrication aggregation. This can be accomplished using a device of the embodiment of either FIGS. 1 or 3. To produce the hollow sphere, a gas is used as the first fluid, and the second fluid is a liquid. The particles containing a gas nucleus, and preferably an air nucleus, may be expelled either into a liquid medium or into a gas medium is shot into a liquid medium, and the spheres cured following expulsion form the pressure chamber. When the first fluid of the invention is a liquid, and the second fluid is a gas, the inertia of the first fluid is low, and the gas abruptly decelerates very soon after it issues from the cusp of the attached droplet. In such an instance, the microjet is so short that it is almost indistinguishable from the stable cusp.

Figure 6:
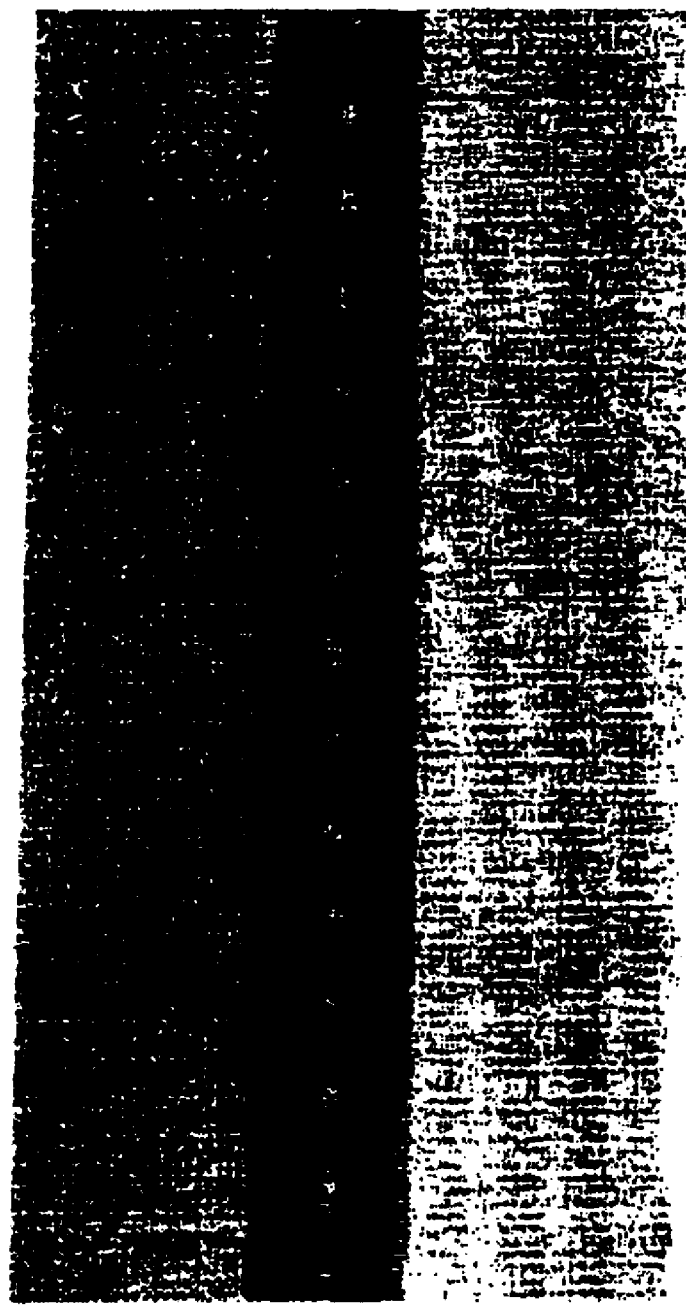
FIG. 6 is a depiction of monodispersed air bubbles surrounded by a coating of liquid dispersed into air.

If a first fluid is a gas, and the second fluid is a liquid, and the particles are expelled into a gaseous atmosphere, a liquid jet with a regularly spaced gaseous formation of particles is formed. The regularity of the particles is such that the liquid jet is deformed in a very regular manner, resulting in a highly monodisperse stream of hollow droplets (FIG. 6). These hollow droplets may be used themselves as assembly components, either in the liquid state or, if desirable, following a curing of the liquid or removal of the liquid component of the second fluid by lyophilization, evaporation, etc. to leave a dry coating on the hollow sphere. Alternatively, the gas inside the hollow particles may be manipulated by appropriate chemical, thermal or mechanical means to expand further upon expulsion form the device, causing the hollow particles to break up into even finer droplets. These finer droplets may then be used as assembly components, or as templates for self assembly as described in the preceding section.

In another example, the embodiment of FIG. 2 can be used, with the fluid of the nucleus as a gas and the fluid of the coating of the particle a liquid that is then cured following expulsion from the pressure chamber. The second fluid used in the invention to focus the first fluid is then preferably a gas, although an immiscible liquid can also be used. Preferably, moisture contained within the coating of the second fluid is removed following expulsion from the pressure chamber, resulting in a dry, hollow sphere of material. These spheres can then be used in microfabrication of larger particles, or may be used for other applications.

A number of different molecules and/or compounds may used to create the assembly components using the method of the invention. A number of potential compounds and their uses are exemplified below.

Assembly components have a potentially high surface area compared to conventional materials, and this can be particularly useful in a number of applications, e.g. catalytic components. Clusters and ultrafine powders can be using the method of the inevention, and the increased surface area of the fine particles affords an excellent degree of control over the total available surface area in self-supported nanophase ensembles. In one example, lightly consolidated, high-surface-area nanophase titanium dioxide with a rutile crystal structure has enhanced chemical reactivity compared to other available forms of titanium dioxide. D. D. Beck and R. W. Siegel, *J. Mater. Res* 7:2840 (1992). More importantly, the nanophase titanium dioxide remains more active that other forms, even after extended exposure to the hydrogen sulfide at 500° C. This enhanced activity results from a combination of unique and controllable features of the nanophase materials, namely its high surface area combined with its rutile structure and its oxygen deficient compositions. The behavior of assembly components comprised of materials such as titanium dioxide should thus have significant future impact in a variety of catalytic and sensor applications.

Clusters of metals, intermetallic compounds, and ceramics can be consolidated using ultrafine-grained polycrystals that are manufactured using the methods of the invention. These clusters can have mechanical properties remarkably different and improved relative to their conventional coarse-granted counterparts. For example, nanophase Cu and Pd assembled from clusters with diameters in the range 5 to 7 nm can have hardness and yield-strength values up to 500% greater than the conventionally produced metal. R. W. Siegel and G. E. Fougere, *Mater. Res. Soc. Sym. Proc.* 362:219 (1995). This greatly increased strength arises from the increased difficulty of the spatially confined grains of nanophase metals to move and create dislocations, which is the defect normally responsible for the relatively easy deformation process in metals.

In ceramics, which are normally difficult to deform and hence very brittle, cluster assembly yields a different benefit. Ceramics and conventionally brittle intermetallics can be rendered ductile (capable of easier deformation) by synthesis from clusters with sizes below about 15 nm. This ductility results from the increased ease with which the ultrafine grains created by the clusters can slide by one another in a process called grain-boundary sliding. Grain-boundary sliding arises from the short diffusion distances required for the necessary local healing of incipient cracks that could allow these materials in their nanophase states to be formed to near-net shapes by means of deformation processing methods previously applicable only to producing ductile metal parts.

Nanocomposites consisting of metallic phases, ceramic and metallic phases (cermets), and ceramic phases in a variety of modulation dimensionalities also have considerably enhanced mechanical properties when produced form extremely small assembly components, including increased strength and fracture toughness. The increased ductility exhibited by nanophase ceramics and intermetallics and the increased strength observed in nanophase metals and nanocomposites should find use in a variety of future technological applications, including bulk materials and coating applications, and especially applications in which wear or corrosion resistance are important design criteria.

Assembly particles may also be used to conduct current in a microfabricated object. Pure nanophase ZnO can exhibit varistor behavior with a small, but usable threshold voltage of 0.1 kV/cm of material for a 60 nm diameter grain size. J. T. Lee et al., *J. Mater. Res.* 10:2295 (1995). This compares with a value of about 4 kV/cm for a conventional, heavily-doped ZnO varistor material, where it is well known that the highly nonlinear 1-V characteristics responsible for the varistor response (i.e., a constant voltage over a wise range of current) stem from grain-boundary conductivity effects. Similarly-doped nanophase ZnO (B, Bi, Co, Cu, Sb, Sn) with 3–10 nm grain sizes can extend the varistor-activity range of the particle up to 30 kV/cm. R. N. Viswanath et al. *Nanostruct. Mater.* 6 (1995). It is possible through assembling components made using the techniques of the present invention to produce ZnO varistors with threshold voltages between at least 0.1 and 30 kV/cm by controlling the particle size and/or the number of assembly components used to create the varistor and, hence, threshold voltages of the manufactured varistors.

Assembly components can also comprise magnetic multilayers, such as those formed by alternating layers of ferromagnetic Fe and Cr, and these multilayer particles are particularly amenable to production using the embodiment of FIG. 2. Such materials are layered in a manner to create an electrical resistance that is significantly decreased (by up to a factor of 2 depending upon the Cr layer thickness) by the application of a magnetic field of 2 T. M. N. Baibach et al., *Phys. Rev. Lett.* 61: 2472 (1988). Such an effect, called giant magnetoresistance (GMR), occurs when the magnetic moments of the neighboring alternating layers (Fe) are arranged in an antiparallel fashion, so that application of the magnetic field overcomes the antiferromagnetic coupling and aligns the layers into a condition of parallel ferromagnetic ordering, strongly reducing the electron scattering in the system. Magnetic materials are already used in the magnetic recording industry as read heads, owning to their lower noise and improved signal handling capabilities. It is now clear that nanostructured magnetic materials have significant application potential in the area of magnetic recording as well as other areas dependent upon stable GMR.

Objects manufactured from assembly components may also have optical properties that make them superior to their larger-scale counterparts. For example, the optical absorption of CdS clusters with diameters in the nanometer size regime is different from that for bulk CdS. The optical absorption edge in isolated, noninteracting clusters in blue shifted to appreciably shorter wavelengths, owing to the effects of quantum confinement in these nanoscale clusters. However, when these clusters are synthesized in zeolite supports with increasing loading, such that they become close enough to begin to interact through quantum tunneling, the absorption edge begins to shift back toward bulk behavior. G. D. Stuckey and J. E. Mac Dougall *Science* 247:669 (1990). A similar effect can be created by changing the sizes of the clusters in colloidal suspensions used as the first fluid of the method of the invention, thereby changing the degree of quantum confinement. Thus, not only do such quantum size effects in assembled clusters provide a basis for verifying out understanding of the electronic structure of condensed matter, they may also provide for engineered optical properties that will have important applications in optical and computing devices.

Particles Containing Discrete Components

Particles containing a selected number of discrete components to be inserted into a particle can be produced using the method and the device of the present invention. The components to be contained in the particles are dispersed in the first fluid in a manner that will control the amount of the component within each given particle. For example, if it is desirable to have one copy of a selected component within each particle, that component is provided in the fluid to be atomized at a rate that allows one copy of the component to be atomized into a single particle. The rate at which the component is focused into the microjet will depend on a number of factors, including the size of the component, the viscosity of the fluid in which the component is dispersed, etc.

Examples of components that can be used in this embodiment of the invention include: biological or biomimetic molecules, e.g. proteins, nucleic acids, cells and biomimetic polymers; informatics-related components, e.g. silicon chips, cadmium sulfide clusters, fiber optic sensors, shape-memory alloys, and intelligent RAM chips; energy conversion particles, e.g. catalysts, conductive metals, ATP, and the like.

Array Production

The method of the invention may also be useful in the production of arrays of microdroplets or more preferably nanodroplets of cells for use in numerous biological and biomedical applications. The solutions or suspensions used to create the nanodroplets preferably contain a relatively uniform concentration of one or a plurality of biological or biomimetic structures. This may include, but is not limited to, nucleic acids, proteins, organelles, portions of cell membrane, synthesized small molecules, engineered protein-like structures, synthesis beads, and/or cells. The cells may be free or bound to a substance, such as a polymer bead. These droplets are preferably comprised of uniform droplets of from 20–200 nanoliters. The nanodroplets are preferably dispersed onto a solid support made of any material suitable for the desired use of the array, and includes materials such as glass, polyurethane, plastic, etc. The spatial segregation of the nanodroplets prevents the mixing of different samples, allowing specific reactions and or activities to be identified with the contents of a particular droplet. See e.g. A. Borchardt et al., Chem Biol 4:961–8 (1997); You et al., Chem Biol 4:969–75 (1997).

The production of arrayed cell nanodroplets using the method of the invention offers several advantages over screening processes using a stochastic arrangement of nanodroplets, including: 1) arrayed nanodroplets prepared they are prepared under milder conditions, allowing assays to be performed with more sensitive cell types, and in particular mammalian cells; 2) the spatially-defined nature of the nanodroplet arrays will make automation of screening, diagnosis, etc. easier; and 3) arrayed nanodroplets have a uniform volume, allowing more accurate dose-response analysis. Cells in the nanodroplets can be adhered to surfaces following dispersion of the liquid onto the solid surface of the array. Proper adhesion of cells may obtained using any method known to those in the art, e.g. pre-treated of the plastic surfaces with extracellular matrix or an adhesion molecule such as fibronectin.

Etching Formulations

Fabrication of articles of manufacture can employ removal of matter to define a desired shape, configuration, and the like. Accordingly, the process of microfabrication may also employ particles that remove matter from existing articles of manufacture. The available size and consistency of particle size produced using the method of the invention may allow a more precise and targeted removal of matter during microfabrication, which may allow the further manipulation of particles produced using either microfabrication or produced using conventional technologies. The removal of the substance will depend on the substance that it is desirable to remove, as will be evident to one skilled in the art.

For example, the manufacture of circuit boards using conventional technology employs solutions for removing metallic copper from the surface of the circuit board, in effect etching into the surface to create a microcircuit pattern. Conventional etching methods utilize solutions containing cupric chloride, ferric chloride, persulfate, hydrogen peroxide, sulfuric acid, an alkali solvent, ammonia and/or ammonia salts as an etching solvent to form printed microcircuits. The efficiency and specificity of the etching process is defined in large part by the particle size of the etching solvent and the pressure at which the etching solvent is applied to the circuit board. For example, U.S. Pat. No. 5,180,465, which is incorporated herein by reference, describes the use of a smaller particle diameter of 100–200 $\mu M$ to more evenly etch a printed circuit board. As circuit boards continue to miniaturize, the ability to target an area with a smaller solvent particle, such as those created using the method of the invention, will allow even finer etching features to be achieved. One or more device of the invention may be used in lieu of conventional nozzles used in a number of etching apparatus known in the art, for example those disclosed in U.S. Pat. Nos. 5,169,477; 5,290,384; 5,378,308; and 5,536,388, to achieve a more finely and consistently etched surface. In addition, the device of the present invention may be used in the microfabrication of microcircuit boards, which may be produced using either top down or bottom up technology.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A method for producing templates for microfabrication, comprising the steps of:
    forcing a first liquid through a channel of a feeding source in a manner which causes the liquid to be expelled from an exit opening;
    forcing a second liquid immiscible with the first liquid through a pressure chamber in a manner which causes the second liquid to exit the pressure chamber from an exit orifice downstream of a flow path of the first liquid expelled from the exit opening of the feeding source;
    wherein a stable first liquid-second liquid interface is maintained and the first liquid forms a stable capillary jet focused to smaller dimensions on the exit orifice of the pressure chamber by the second liquid.

2. The method of claim 1, wherein the feeding source is a cylindrical channel and the first liquid is expelled from an exit opening having a diameter in the range of from about 0.002 to about 2 mm and wherein the opening in the pressure chamber has a diameter in the range of about 0.002 to about 2 mm and is positioned directly in front of a flow path of the exit opening of the channel.

3. The method of claim 1, wherein the exit opening has a diameter in the range of from about 100 nm to about 0.1 mm, and
    wherein the exit opening of the feeding source of the first liquid is separated by a distance of from about 0.002 mm to about 2 mm from the exit opening in the pressure chamber.

4. A method for producing assembly components for microfabrication, comprising the steps of:
    forcing a liquid through a channel of a feeding source in a manner which causes the liquid to be expelled from an exit opening;
    forcing a gas through a pressure chamber in a manner which causes the gas to exit the pressure chamber from an exit orifice downstream of a flow path of the liquid expelled from the exit opening of the feeding source;
    wherein a stable liquid-gas interface is maintained and the liquid forms a stable capillary jet focused to smaller dimensions on the exit orifice of the pressure chamber by the second fluid.

5. The method of claim 4, wherein the feeding source is a cylindrical channel and the liquid is expelled from an exit opening having a diameter in the range of from about 0.002 to about 2 mm and wherein the opening in the pressure chamber has a diameter in the range of about 0.002 to about 2 mm and is positioned directly in front of a flow path of the exit opening of the channel.

6. The method of claim 4, wherein the exit opening has a diameter in the range of from about 100 nm to about 0.1 mm, and
    wherein the exit opening of the feeding source of the liquid is separated by a distance of from about 0.002 mm to about 2 mm from the exit opening in the pressure chamber.

7. The method of claim 4, wherein the jet exits the pressure chamber and disassociates into particles, and wherein each particle contains a discrete component.

8. The method of claim 7, wherein the discrete component forms a product selected from the group consisting of:

biological molecules, proteins, nucleic acids, cells, biomimetic molecules, silicon chips, cadmium sulfide clusters, titanium dioxide crystals, fiber optic sensors, shape-memory alloys, intelligent RAM chips, catalysts, clusters of conductive metals, and ATP.

9. A method of creating an array, comprising the steps of:
forcing a liquid comprising a biological or biomimetic molecule through a channel of a feeding source in a manner which causes the liquid to form a stream which is expelled from an exit opening;

forcing a gas through a pressure chamber in a manner which causes the gas to exit the pressure chamber from an exit orifice downstream of a flow path of the liquid stream expelled from the exit opening of the feeding source and where the stream disassociates and forms particles on exiting the pressure chamber; and directing the particles onto a solid support surface;

wherein a stable liquid-gas interface is maintained and the liquid stream forms a stable capillary jet focused to smaller dimensions on the exit orifice of the pressure chamber by the gas.

10. The method of claim 9, wherein gas from the pressure chamber surrounds liquid exiting the feeding source outlet which liquid is drawn into the orifice concentrically being focused by the gas flowing out of the outlet, and further wherein 90% or more of the particles formed are uniform in size to the extent of having a relative size standard deviation of 3 to 30%.

11. A method for etching a coated surface of an object, comprising the steps of:

forcing liquid etching solution through a channel of a feeding source in a manner which causes the liquid to be expelled from an exit opening;

forcing a gas through a pressure chamber in a manner which causes the gas to exit the pressure chamber from an exit orifice downstream of a flow path of the liquid stream expelled from the exit opening of the feeding source and wherein the stream disassociates and forms particles on exiting the pressure chamber; and directing the particles to a selected area of the object;

wherein a stable liquid-gas interface is maintained and the liquid stream of etching solution forms a stable capillary jet focused to smaller dimensions on the exit orifice of the pressure chamber by the gas; and wherein the particles directed to the selected area results in removal of the coated surface in the selected area.

12. The method of claim 11, further comprising:

flushing the etching solution from the surface of the object with a solution that is non-reactive with the coated surface.

13. The method of claim 11, wherein the surface of the object is coated with copper, and wherein the etching fluid is an aqueous solution containing a compound selected from the group consisting of: cupric chloride, ferric chloride, persulfate, hydrogen peroxide, sulfuric acid, an alkali solvent, ammonia and ammonia salts.

* * * * *